United States Patent [19]

Miyazaki et al.

[11] Patent Number: 5,380,700
[45] Date of Patent: Jan. 10, 1995

[54] PYRIDINE DERIVATIVES, HERBICIDAL COMPOSITION CONTAINING THE SAME, AND METHOD FOR KILLING WEEDS

[75] Inventors: Masahiro Miyazaki; Masafumi Matsuzawa; Keiji Toriyabe, all of Shizuoka; Michiya Hirata, Kashiwa, all of Japan

[73] Assignees: Kumiai Chemical Industries Co., Ltd.; Ihara Chemical Industries Co., Ltd., both of Tokyo, Japan

[21] Appl. No.: 996,042

[22] Filed: Dec. 23, 1992

Related U.S. Application Data

[63] Continuation-in-part of Ser. No. 927,281, Sep. 17, 1992.

[30] Foreign Application Priority Data

Mar. 26, 1991 [JP] Japan ................................. 3-84556

[51] Int. Cl.$^6$ .................. C07D 401/02; C07D 401/14; C07D 403/02; A01N 43/54
[52] U.S. Cl. .................... 504/239; 504/242; 504/243; 544/296; 544/300; 544/310; 544/316; 544/317; 544/318
[58] Field of Search ............... 544/300, 310, 316, 317, 544/318, 296; 504/239, 243, 242

[56] References Cited

FOREIGN PATENT DOCUMENTS 0472925  3/1992  European Pat. Off. .
7699  2/1970  France .

OTHER PUBLICATIONS

Heinemann et al., Chem. Abstracts, vol. 116(13), Abst. No. 128,976(d), Mar. 30, 1992.
Annales Pharmaceutiques Francaises, vol. 38, No. 3, pp. 267–270, 1980, J. C. Jamoulle, et al., "Etude De La Relation Entre La Structure Chimique Et L'Activite Antimitotique D'Une Serie Nouvelle D'Arylthioethers Pyrimidiniques".

Primary Examiner—Alan L. Rotman
Attorney, Agent, or Firm—Oblon, Spivak, McClelland, Maier, & Neustadt

[57] ABSTRACT

The present invention provides a novel pyridine derivative having the following general formula and its salt:

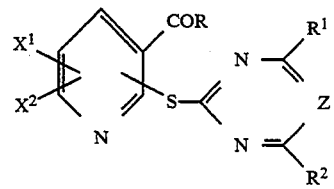

wherein R is a hydrogen atom, a hydroxyl group, an alkoxy group, an alkoxyalkoxy group, and derivatives;

$R^1$ and $R^2$ may be the same or different, and are a hydrogen atom, an alkoxy group, a halogen atom, an alkylamino group, a dialkylamino group;

Z is a methine group or a nitrogen atom;

$X^1$ is an acylamino group, a cycloalkyl group, a halogen-substituted alkoxy group, an alkenyloxy group, an alkynyloxy group, an alkoxycarbonyl group, an alkylamino group, a dialkylamino group, a phenyl group.

The pyridine derivative and its salt of the present invention achieve an excellent herbicidal effect on annual and perennial weeds growing in paddy fields and upland fields at a very small dosage.

The pyridine derivative and its salt of the present invention have safety to rice, wheat, cotton and corn, and can be suitably applied as a herbicide to a field where these plants are cultivated.

9 Claims, No Drawings

PYRIDINE DERIVATIVES, HERBICIDAL COMPOSITION CONTAINING THE SAME, AND METHOD FOR KILLING WEEDS

CROSS-REFERENCE

This application is a continuation-in-part of U.S. patent application Ser. No. 07/927,281 filed Sep. 17, 1992.

BACKGROUND OF THE INVENTION

1. Field of the Invention

The present invention relates to a novel pyridine derivative and its salt, a method for preparing the same, a herbicidal composition containing the same as an effective ingredient, and a method for killing weeds.

2. Discussion of Background

Heretofore, as a pyridine carboxylic acid derivative having a herbicidal activity, there were known 3-(4,6-dimethoxypyrimidin-2-yl)oxypicolinic acid derivative (Japanese Unexamined Patent Publication No. 84/1989), pyrimidyloxypicolinic acid derivative and pyrimidyloxyisonicotinic acid derivative (Japanese Unexamined Patent Publication No. 121973/1990 and 149567/1990).

However, these references do not describe a nicotinic acid derivative having a heterocyclic ring-containing substituent at the 2-position as in the compound of the present invention.

Heretofore, many herbicides have been developed, and have contributed to the saving of energy for the agricultural operations and to the improvement of the production efficiency. However, in their practical use, such herbicides have various problems. For example, a herbicide achieving a herbicidal effect specially at a low dose is desired in view of environmental problems. Particularly, a desirable herbicide should have a herbicidal effect for killing perennial weeds such as johnsongrass (*Sorghum halepense*) and purple nutsedge (*Cyperus rotundus*) which are widely distributed on agricultural lands throughout the world and are hardly killed. Furthermore, a herbicide having a satisfactory selectivity and safety to crop plants is particularly desired in respect of agricultural management.

Up to now, the known compounds as described in the above references do not always have satisfactory herbicidal effects.

The present inventors have conducted extensive research on nicotinic acid derivatives with an aim to develop a compound having a satisfactory herbicidal activity, and as a result, have found that the pyridine derivative of the present invention which is a nicotinic acid derivative having a heterocyclic ring-containing substituent at the 2-position, has an excellent herbicidal activity for killing annual and perennial weeds including gramineous weeds, cyperaceous weeds and broadleaf weeds by water treatment of rice fields and soil treatment or foliage treatment of upland fields, and also has a satisfactory safety to crop plants including rice, wheat and the like. The present invention has been accomplished on the basis of this discovery.

DISCLOSURE OF THE INVENTION

The pyridine derivative of the present invention is defined by the general formula (I):

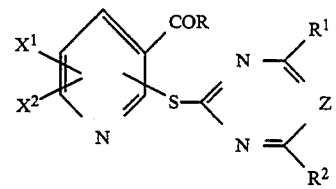

wherein R is a hydrogen atom, a hydroxyl group, an alkoxy group, an alkoxyalkoxy group, an acyloxyalkoxy group, a benzyloxy group which may be substituted, a trimethylsilylethoxy group, an alkylsulfonylamino group, an alkylthio group, a phenoxy group which may be substituted, a phenylthio group which may be substituted or an imidazolyl group;

$R^1$ and $R^2$ may be the same or different, and are a hydrogen atom, an alkoxy group, a halogen atom, an alkylamino group, a dialkylamino group, a halogen-substituted alkoxy group or an alkyl group;

Z is a methine group or a nitrogen atom;

$X^x$ is an acylamino group, a cycloalkyl group, a halogen-substituted alkoxy group, an alkenyloxy group, an alkynyloxy group, an alkoxycarbonyl group, an alkylamino group, a dialkylamino group, a phenyl group, a substituted phenyl group, a benzyloxy group which may be substituted, a benzylthio group which may be substituted, a benzyl group which may be substituted, a phenoxy group which may be substituted, a phenylthio group which may be substituted, an alkoxyiminoalkyl group, an acyl group, an alkylthio group, an arylamino group which may be substituted, a carboxyl group, a benzoylamino group, or a group having the formula,

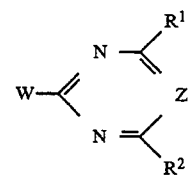

(wherein $R^1$, $R^2$ and Z are as defined above, and W is an oxygen atom, a sulfur atom, a NH group or a group of the formula, >NC(O)B (wherein B is a hydrogen atom or an alkoxy group)); and $X^2$ is a hydrogen atom, a halogen atom, a halogen-substituted alkyl group, an alkyl group, a cycloalkyl group, a haloalkoxy group, an alkenyloxy group, an alkynyloxy group, an alkoxycarbonyl group, an alkoxy group, an alkylamino group, a dialkylamino group, an acylamino group, a phenyl group, a substituted phenyl group, a benzyloxy group which may be substituted, a benzylthio group which may be substituted, a benzyl group which may be substituted, a phenoxy group which may be substituted, a phenylthio group which may be substituted, an alkoxyiminoalkyl group, an acyl group, an alkylthio group, an arylamino group which may be substituted, a carboxyl group, a benzoylamino group or a group having the formula,

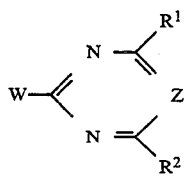

(wherein $R^1$, $R^2$, W and Z are as defined above).

The present invention relates to a pyridine derivative and its salt.

Also, the present invention further relates to a method for preparing the pyridine derivative, a herbicidal composition containing the pyridine derivative or its salt as an effective ingredient and a method for killing weeds.

In the general formula (I), examples of the alkoxy group of R include a straight-chain or branched $C_1 \sim C_7$ alkoxy group such as a methoxy group, an ethoxy group, a n-propoxy group, an isopropoxy group, a n-butoxy group, an isobutoxy group, a s-butoxy group, a t-butoxy group, a n-pentyloxy group, an isopentyloxy group, a s-pentyloxy group, a t-pentyloxy group, a n-hexyloxy group, a 2,2-dimethylpropoxy group, a 2-methylbutoxy group, a 2-ethylbutoxy group, a 3,3-dimethylbutoxy group, and a 1,3,3-trimethylbutoxy group.

Examples of the alkoxy group of $R^1$ and $R^2$ are as defined in the above alkoxy group of R. Examples of the halogen atom include chlorine, bromine, fluorine and iodine. Examples of the alkylamino group include a straight-chain or branched $C_1 \sim C_3$ alkylamino group such as a methylamino group, an ethylamino group, a n-propylamino group and an isopropylamino group. Examples of the dialkylamino group include a straight-chain or branched $C_1 \sim C_3$ dialkylamino group such as a dimethylamino group, a diethylamino group, a methylethylamino group, a di-n-propylamino group and a diisopropylamino group. Examples of the haloalkoxy group include a straight-chain or branched $C_1 \sim C_7$ haloalkoxy group having a part or the whole part of the alkoxy group substituted with the above-mentioned halogen atoms, such as a difluoromethoxy group and a chloromethoxy group. Examples of the alkyl group include a straight-chain or branched $C_1 \sim C_7$ alkyl group such as a methyl group, an ethyl group, n-propyl group, an isopropyl group, a n-butyl group, an isobutyl group, a s-butyl group, a t-butyl group, a n-pentyl group, an isopentyl group, a s-pentyl group, a t-pentyl group, a n-hexyl group, a 2,2-dimethylpropyl group, a 2-methylbutyl group, a 2-ethylbutyl group, a 3,3-dimethylbutyl group and a 1,3,3-trimethylbutyl group.

Examples of the halogen atom, alkylamino group and dialkylamino group of X are as defined in the above-mentioned halogen atom, alkylamino group and dialkylamino group of $R^1$ and $R^2$. Examples of the halogen-substituted alkyl group include a halogen-substituted alkyl group having a part or the whole part of a straight-chain or branched $C_1 \sim C_3$ alkyl group substituted with the above-mentioned halogen atoms, such as a difluoromethyl group, a chloromethyl group and a tribromomethyl group. Examples of the alkyl group are as defined in the above-mentioned alkyl group of $R^1$ and $R^2$. Examples of the alkoxy group are as defined in the above-mentioned alkoxy group of $R^1$ and $R^2$.

Examples of the haloalkoxy group are as defined in the above-mentioned haloalkoxy group of $R^1$ and $R^2$.

Examples of the cycloalkyl group include a $C_3 \sim C_7$ cycloalkyl group such as a cyclopropyl group, a cyclopentyl group and a cyclohexyl group.

Examples of the alkenyloxy and alkynyloxy groups include $C_2 \sim C_8$ alkenyloxy and alkynyloxy groups.

Examples of the substituted phenyl group include a substituted phenyl group, a part or the whole part of the phenyl group being substituted with the above-mentioned halogen, lower alkyl, lower alkoxy, alkylamino, dialkylamino, halogen-substituted alkyl, haloalkoxy, nitro, hydroxy, alkoxyalkoxy, alkoxycarbonylalkoxy, alkylthioalkoxy, benzyloxy, cyano, phenoxy, substituted phenoxy, alkylthio, alkoxyalkyl or ethynyl group, such as a p-chlorophenyl group and a 3-tolyl group. Examples of a preferable compound include a compound of the general formula (I) wherein R is a hydroxyl group, a methoxy group, an ethoxy group, a benzyloxy group, an ethoxymethoxy group, a pivaloyloxymethoxy group or a trimethylsilylethoxy group; $R^1$ and $R^2$ are the same or different and are a hydrogen atom, a chlorine atom, a methyl group, a methoxy group, a dimethylamino group or a halogen-substituted methoxy group; $X^1$ is a phenyl group, a halogen-substituted phenyl group, a methyl-substituted phenyl group, a methoxy-substituted phenyl group or a mono or dimethylamino group; $X^2$ is a hydrogen atom; Z is a methine group or a nitrogen atom.

The compound of the present invention of the general formula (I) can be prepared, for example, by the following preparation method, but the present invention is not limited to these methods.

PREPARATION METHOD 1

Reaction Formula 1

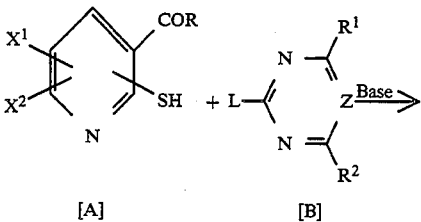

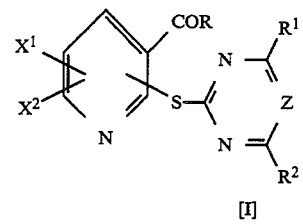

(wherein L is a halogen atom, an alkylsulfonyl group, a benzylsulfonyl group which may be substituted, an alkylsulfonate group, a haloalkylsulfonate group or a benzylsulfonate group which may be substituted; and $X^1$, $X^2$ R, $R^1$ $R^2$ and Z are as defined above.)

The compound of the general formula (I) can be prepared by reacting a compound of the formula (A), with a compound of the formula (B) in the presence of a base having an amount of at least equivalent amount in an appropriate solvent at a temperature in the range from room temperature to the boiling point of the solvent for from 0.5 to 24 hours.

Here, as the base, there may be employed an alkali metal such as lithium metal, sodium metal or potassium metal, organic lithium reagents such as n-butyl lithium or lithium diisopropylamide (LDA); an alkali metal or an alkaline earth metal hydride such as sodium hydride, potassium hydride or calcium hydride; an alkali metal alkoxide such as potassium t-butoxide; an alkali metal carbonate such as sodium carbonate or potassium carbonate; or a metal hydroxide such as sodium hydroxide or potassium hydroxide.

As the solvent, there may be employed a hydrocarbon solvent such as hexane, benzene, toluene or xylene; a halogenated hydrocarbon solvent such as dichloromethane or chloroform; an ether solvent such as diethyl ether, tetrahydrofuran or 1,4-dioxane; an ester solvent such as methyl acetate and ethyl acetate; a ketone solvent such as acetone and ethyl methyl ketone; an aprotic polar solvent such as N,N-dimethylformamide, N,N-dimethylacetamide and dimethylsulfoxide; and others such as acetonitrile or the like.

The compound of the formula (A) can be prepared in the accordance with the methods disclosed in "Journal of Medicinal Chemistry" (vol. 6, p. 294, 1963; and vol. 7, p. 17, 1964), "Berichte" (74B, p. 1111, 1941), "Liebigs Ann. Chem." (371, 1979) and the like, but can also be prepared by the following method.

Reaction Formula 2-1

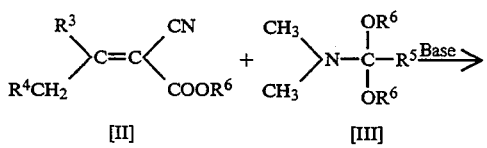

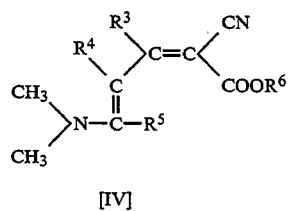

Reaction Formula 2-2

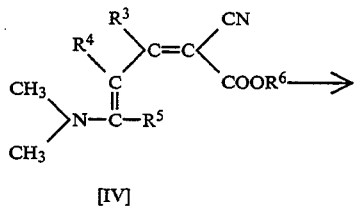

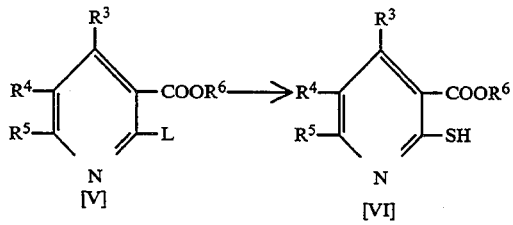

(wherein $R^3$ $R^4$ and $R^5$ are the same or different, and are a hydrogen atom, a lower alkyl group, a lower alkoxy group, an alkylamino group, a dialkylamino group, a phenyl group or a substituted phenyl group; $R^6$ is a hydrogen atom or an alkyl group; and L is as defined above.)

The compound of the formula (IV) can be prepared by heating a compound of the formula (II) and an acetal compound of the formula (III) in the presence or absence of an inorganic or organic base for from 0.1 to 10 hours in an appropriate solvent including an alcohol such as methanol or ethanol, an ether such as tetrahydrofuran, an aprotic polar solvent such as N,N-dimethylformamide or acetonitrile ("Archiv der Pharmazie" vol. 318, p. 481, 1985).

Also, the compound of the formula (V) can be prepared by reacting the compound of the formula (IV) with hydrogen bromide or hydrogen chloride gas in an inert solvent such as dichloroethane or toluene or acetic acid within a temperature range from 0° C. to the boiling point of the solvent, preferably from 10° C. to 50° C.

Furthermore, the compound of the formula (VI) can be prepared by reacting the above prepared compound of the formula (V) with thiourea within a temperature range from 50° C. to 120° C. for 0.5 to 10 hours in the presence of water and a mineral acid such as hydrochloric acid or sulfuric acid, treating the resultant product with an alkaline material such as sodium hydroxide or potassium hydroxide, and then acidifying the resultant product with an acid such as hydrochloric acid (see Japanese Unexamined Patent Publication No. 275562/1989). The product thus obtained contains a small amount of sulfide and disulfide in addition to the aimed thiol compound.

PREPARATION METHOD 2

Reaction Formula 3

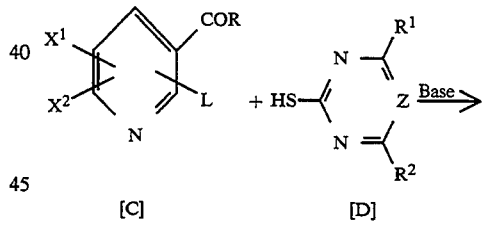

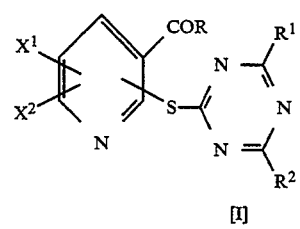

(wherein L, $X^1$, $X^2$, R, $R^1$, $R^2$, and Z are as defined above.)

The compound of the formula (I) can also be prepared by reacting a compound of the formula (C) with a compound of the formula (D) in the presence of a base having an amount of at least equivalent amount in an appropriate solvent for 0.5 to 24 hours within a temperature range from room temperature to the boiling point of the solvent. The base and the solvent used may be the same in the above Preparation Method 1.

PREPARATION METHOD 3

Reaction Formula 4

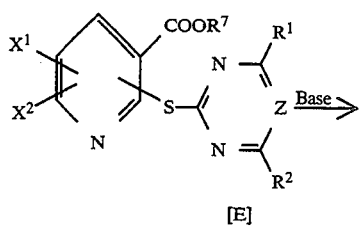

[E]

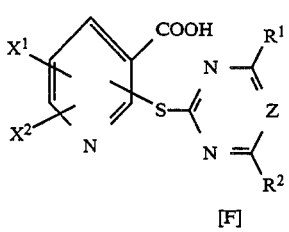

[F]

(wherein $R^7$ is an alkyl group or a trimethylsilylethyl group; and $X^1$, $X^2$, Z, $R^1$ $R^2$ are as defined above.)

The compound of the formula (F) can be prepared by reacting the compound of the formula (E) in the presence of a base having an amount of at least equivalent amount in an appropriate solvent such as water or a solvent containing water for 0.5 to 24 hours at a temperature of from room temperature to the boiling point of the solvent and then acidifying the resultant product.

Here, as the base, there may be employed a metal hydroxide such as sodium hydroxide or potassium hydroxide; a carbonate such as sodium carbonate or potassium carbonate; a hydrogen carbonate such as sodium hydrogen carbonate or potassium hydrogen carbonate. In the case of trimethylsilyl ethyl ester, the compound of the formula (E) may be prepared by the reaction with tetrabutylammonium fluoride or potassium fluoride.

As the solvent, there may be employed a hydrocarbon solvent such as hexane; a halogenated hydrocarbon solvent such as dichloromethane or chloroform; an alcohol solvent such as methanol, ethanol or 2-propanol; an ether solvent such as diethyl ether, tetrahydrofuran or 1,4-dioxane; a ketone solvent such as acetone or ethyl methyl ketone; an aprotic polar solvent such as N,N-dimethylformamide, N,N-dimethylacetamide or dimethylsulfoxide; and others such as acetonitrile or the like.

PREPARATION METHOD 4

Reaction Formula 5

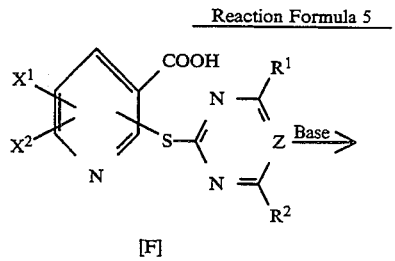

[F]

-continued
Reaction Formula 5

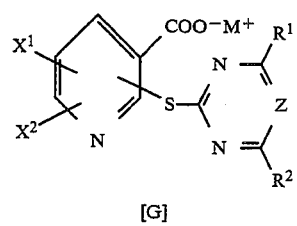

[G]

(wherein M+ is 1 equivalent amount of alkali metal, alkaline earth metal, ammonium or organic ammonium ion; and $X^1$, $X^2$, Z, $R^1$ and $R^2$ are as defined above.)

The compound of the formula (G) can be prepared by reacting the compound of the formula (F) with an equivalent amount of a base in an appropriate solvent for 0.5 to 24 hours within a temperature range from room temperature to the boiling point of the solvent.

Here, as the base, there may be employed an alkali metal hydride such as sodium hydride and potassium hydride; an alkali metal alkoxide such as sodium methoxide or sodium ethoxide; an alkali metal or alkaline earth metal carbonate such as sodium carbonate and calcium carbonate; an alkali metal or alkaline earth metal hydroxide such as sodium hydroxide, potassium hydroxide or calcium hydroxide; an alkali metal hydrogencarbonate such as sodium hydrogencarbonate and potassium hydrogencarbonate; and an organic amine such as isopropylamine.

As the solvent, there may be employed a hydrocarbon solvent such as benzene, toluene and xylene; a halogenated hydrocarbon solvent such as dichloromethane or chloroform; an alcohol solvent such as methanol, ethanol and 2-propanol; an ether solvent such as diethyl ether, tetrahydrofuran or dioxane; an aprotic polar solvent such as N,N-dimethylacetamide or dimethylsulfoxide; and others such as acetonitrile, water or the like.

PREPARATION METHOD 5

Reaction Formula 6

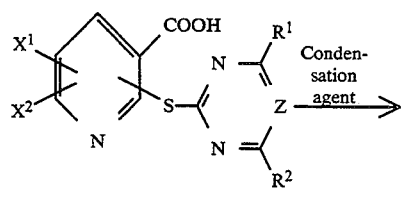

[F]

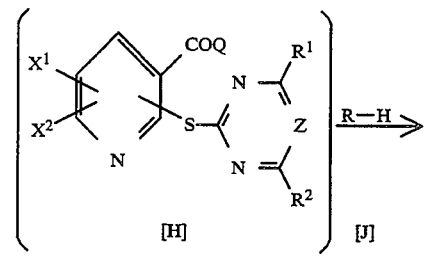

[H]     [J]

-continued
Reaction Formula 6

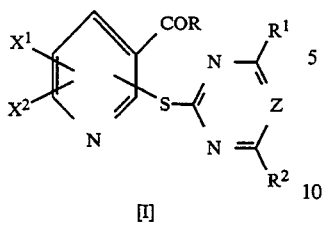

(wherein Q is a halogen atom, a cyano group, an imidazolyl group or a substituted amidinoxy group; and R, $R^1$, $R^2$, $X^1$, $X^2$ and Z are as defined above.)

The intermediate compound of the formula (H) for preparing the compound of the present invention of the formula (I) can be prepared by reacting the compound of the formula (F) with a condensation agent having an amount of at least equivalent amount in an appropriate solvent for 0.5 to 24 hours within a temperature range from −10° C. to the boiling point of the solvent. The intermediate compound thus prepared may be separated or may not be separated, and the compound of the formula (I) can be prepared by reacting the intermediate compound with a compound of the formula (J) and a base having an amount of at least equivalent amount in an appropriate solvent for 0.5 to 24 hours within a temperature range from −10° C. to the boiling point of the solvent.

As the condensation agent, there may be employed a thionyl chloride, oxalic acid dichloride, chlorocarbonic acid ester, carbonyldiimidazole, cyanophosphoric acid ester, carbodiimide or the like. Here, the base and the solvent may be the same as used in the Method 1 as described above.

PREPARATION METHOD 6

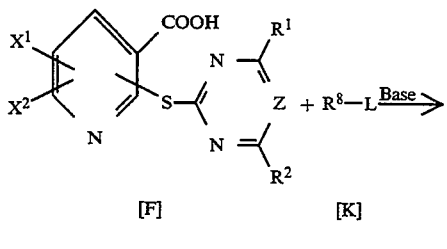

(wherein $R^8$ is an alkyl group, an alkoxyalkyl group, an acyloxyalkyl group or a benzyl group which may be substituted; and $R^1$, $R^2$, L, $X^1$, $X^2$ and Z are as defined above.)

The compound of the formula (I) can be prepared by reacting the compound of the formula (F) with the compound of the formula (K) in the presence of one equivalent or more of base in an appropriate solvent for 0.5 to 24 hours within a temperature range from −10° C. to the boiling point of the solvent. Here, the base and the solvent may be the same as used in the Method 1 as described above.

[BEST MODE FOR CARRYING OUT THE INVENTION]

In the following, the method for preparing the compound of the present invention is more concretely explained by giving Examples.

PREPARATION EXAMPLE 1

Synthesis of methyl 4-(4-chlorophenyl)-2-(4,6-dimethoxypyrimidin-2-ylthio)nicotinate (Compound No. 8)

A mixture of 73.9 g (0.24 mol) of 2-bromo-4-(4-clorophenyl)nicotinic acid and 22.0 g (0.29 mol) of thiourea in 100 ml of 5% HCl and 150 ml of acetic acid was stirred at 100° C. for 2 hours. The mixture was poured into water and 400 ml of 50% sodium hydroxide was added to the resultant mixture, and the mixture was stirred at room temperature for 30 minutes. The mixture was then acidified with 20% HCl, and the crystal thus precipitated was filtrated out and washed with water. The washed crystal was then dried to obtain a crude crystal of 2-mercapto-4-(4-chlorophenyl)nicotinic acid.

The crude crystal thus obtained, 66.0 g (0.30 mol) of 4,6-dimethoxy-2-methylsulfonylpyrimidine and 104.0 g (0.75 mol) of potassium carbonate were dissolved in 500 ml of dimethylsulfoxide, and stirred at 80° C. for 2 hours. After the temperature was restored to room temperature, 68.0 g (0.48 mol) of methyl iodide was added to the reaction mixture, and the resultant reaction mixture was stirred at room temperature for 30 minutes. The reaction mixture was then poured into water, and extracted with 1 l of ethyl acetate. The extract was washed with water and a saturated aqueous solution of sodium chloride, and dried over anhydrous sodium sulfate, and concentrated. The concentrate was purified by silica gel column chromatography (eluting solvent: ethyl acetate/hexane=¼) to obtain 19.0 g of a white crystal of the aimed product.

Yield: 19.2%, Melting point: 138°–141.5° C.

PREPARATION EXAMPLE 2

Synthesis of 4-(4-chlorophenyl)-2-(4,6-dimethoxypyrimidin-2-ylthio)nicotinic acid (Compound No. 9)

16.8 g (0,040 mol) of methyl 4-(4-chlorophenyl)-2-(4,6-dimethoxypyrimidin-2-ylthio)nicotinate was dissolved in 150 ml of dimethylsulfoxide, and 35 ml (0,070 mol) of 2N sodium hydroxide added with stirring at 60° C. After stirring at 60° C. for 30 minutes, the mixture was poured into water, and washed twice with ethyl acetate. The aqueous layer was acidified with 10% hydrochloric acid, and extracted with 500 ml of ethyl acetate. The extract was washed with water and a saturated aqueous solution of sodium chloride, and dried over anhydrous sodium sulfate, and concentrated. The concentrate was washed with methanol and isopropyl ether to obtain 11.5 g of a white crystal of the aimed product.

Yield: 70.8%, Melting point: 219°–223° C.

PREPARATION EXAMPLE 3

Synthesis of pivaloyloxymethyl 4-(4-fluorophenyl)-2-(4,6-dimethoxypyrimidin-2-ylthio)nicotinate (Compound No. 19)

A mixture of 0.70 g (0.0019 mol) of 4-(4-fluorophenyl)-2-(4,6-dimethoxypyrimidin-2-ylthio)nicotinic acid and 0.50 g (0.0036 mol) of potassium carbonate in 10 ml of N,N-dimethylformamide was stirred at room temperature for 1 hour. Thereafter, 0.34 g (0.0022 mol) of chloromethyl pivalate was further added to the resultant mixture, and the mixture was stirred at room temperature for 2 hours. The mixture was then poured into water, and extracted with 50 ml of ethyl acetate. The extract was washed with water and a saturated aqueous solution of sodium chloride, and dried over anhydrous sodium sulfate, and concentrated. The concentrate was purified by silica gel column chromatography (eluting solvent: ethyl acetate/hexane=½) to obtain 0.81 g of a yellowish thick syrup-like aimed product.

Yield: 88 0%, Refractive index ($n_D^{20}$): 1.5615

PREPARATION EXAMPLE 4

Synthesis of methyl 4-(4-isopropoxyphenyl)-2-(4,6-dimethylpyrimidin-2-ylthio)nicotinate (Compound No. 74)

20.0 g (0.059 mol) of 2-bromo-4-(4-isopropoxyphenyl)nicotinic acid and 5.5 g (0.072 mol) of thiourea were dissolved in 40 ml of 5% HCl and 60 ml of acetic acid, and stirred at 100° C. for 2 hours. The reaction mixture was poured into water, and 200 ml of 50% sodium hydroxide was added thereto, and the mixture was stirred at room temperature for 30 minutes. The mixture was then acidified with 20% HCl and the thus precipitated was filtrated out and washed with water and then dried. The above synthesized crude crystal [2-mercapto-4-(4-isopropoxyphenyl)nicotinic acid] and 11.1 g (0.060 mol) of 4,6-dimethyl-2-methylsulfonylpyrimidine, and 25.0 g (0.18 mol) of potassium carbonate were dissolved in 200 ml of dimethylsulfoxide and stirred at 80° C. for 2 hours. After restoring the temperature to room temperature, 16.8 g (0.12 mol) of methyl iodide was added to the reaction mixture, and the mixture was stirred at room temperature for 30 minutes. The reaction mixture was then poured into water, and was extracted with 500 ml of ethyl acetate. The organic layer was washed with water and a saturated aqueous solution of sodium chloride, and dried over anhydrous sodium sulfate, and concentrated. The concentrate was purified by silica gel column chromatography (eluting solvent: ethyl acetate/hexane=½) to obtain 6.5 g of a light-yellowish thick syrup-like aimed product.

Yield: 26.7%, Refractive index ($n_D^{20}$): 1.5965

PREPARATION EXAMPLE 5

Synthesis of sodium 4-(4-chlorophenyl)-2-(4,6-dimethoxypyrimidin-2-ylthio)nicotinate (Compound No. 167)

To a solution of 0.50 g (0.0012 mol) of 4-(4-chlorophenyl)-2-(4,6-dimethoxylpyrimidin-2ylthio)nicotinic acid in 7 ml of ethanol was added 0.30 g (0.0016 mol) of methanol solution of 28% sodium methylate at room temperature. After addition, the mixture was further stirred at room temperature for 20 minutes. The crystal thus precipitated was filtrated, and washed with ethanol and dried to obtain 0.46 g of a white powder of the aimed product.

Yield: 86.0%, Melting point: 244°–247° C.

PREPARATION EXAMPLE 6

Synthesis of 4-(3-chlorophenyl)-2-(4,6-dimethoxypyrimidin-2-ylthio)-N-methylsulfonylnicotinamide (Compound No. 161)

To a solution of 3.0 g (0.0074 mol) of 4-(3-chlorophenyl)-2-(4,6-dimethoxypyrimidin-2-ylthio)nicotinic acid in 30 ml of N,N-dimethylformamide was added 1.50 g (0.0093 mol) of carbonyldiimidazole with stirring, and the mixture was stirred at room temperature for 24 hours. To a suspension of 0.60 g (0.0015 mol) of 60% sodium hydride in 30 ml of N,N-dimethylformamide was added 1.8 g (0.0019 mol) of methanesulfonamide and stirred at 80° C. for 2 hours. Thereafter, the above prepared N,N-dimethylformamide solution of carbonylimidazole of nicotinic acid was added thereto at room temperature, and the mixture was stirred at 80° C. for 2 hours. The reaction mixture was then poured into water, and washed with 50 ml of ethyl acetate. Thereafter, the aqueous layer was acidified with 10% HCl, and extracted with 100 ml of ethyl acetate. The organic layer was washed with water and a saturated aqueous solution of sodium chloride, and dried over anhydrous sodium sulfate, filtrated and concentrated. The concentrate was purified by silica gel column chromatography (eluting solvent: ethyl acetate/hexane=1/1) to obtain 3.0 g of a light-yellowish glass-like aimed product.

Yield: 81.3%, Melting point: 54°–58° C.

REFERENCE EXAMPLE 1

Synthesis of 1-cyano-1-methoxycarbonyl-2-(4-dimethylamino)-2-(4-methoxyphenyl)-1,3-butadiene (Intermediate No. 5)

85.0 g (0.44 mol) of 1-cyano-1-methoxycarbonyl-2-(4-methoxyphenyl)-1-propylene and 79 g of 1,1-dimethoxytrimethylamine (0.66 mol) were dissolved in 200 ml of methanol and refluxed for 30 minutes with stirring. The reaction mixture was cooled with ice water to precipitate a crystal, which was then filtrated out. The crystal thus obtained was washed three times with 100 ml of methanol, and dried to obtain 103.6 g of a greenish yellow aimed product.

Yield: 81.4%, Melting point: 175°–178° C.

REFERENCE EXAMPLE 2

Synthesis of methyl 2-bromo-4-(4-chlorophenyl)nicotinate (Intermediate No. 56)

To a solution of 80.0 g (0.28 mol) of 1-cyano-1-methoxycarbonyl-4-(N,N-dimethylamino)-2-(4-chlorophenyl)-1,3-butadiene in 100 ml of acetic acid, an acetic acid solution of 25% HBr was then gradually added dropwise at room temperature with stirring. After the dropwise addition, the resultant mixture was stirred at room temperature for 3 hours. The reaction mixture was then poured into ice water to precipitate a crystal. The crystal thus precipitated was filtrated out and washed with water and dried to obtain 75.0 g of a white crystal of the aimed product.

Yield: 83.5%, Melting point: 73°–76° C.

REFERENCE EXAMPLE 3

Synthesis of 2-bromo-4-(4-chlorophenyl)nicotinic acid (Intermediate No. 57)

To a solution of 50.0 g (0.15 mol) of methyl 2-bromo-4-(4-chlorophenyl)nicotinate in 300 ml of dimethylsulfoxide, 60 ml of 30% sodium hydroxide was added and stirred at 80° C. for 3 hours. The mixture was then poured into water and washed with 300 ml of ethyl acetate. Thereafter, the aqueous layer was acidified with 10% HCl to precipitate a crystal, which was then filtrated out. The crystal thus precipitated was washed with water and isopropyl ether, and dried to obtain 41.0 g of a white crystal of the aimed product.

Yield: 85.7%, Melting point: 204°-208° C.

In the following, examples of the compound of the present invention thus obtained are illustrated in Table 1. The abbreviation marks in the Table respectively mean the following groups.

Compound Nos. given in the Table will be referred to the subsequent description in the specification.

Pym: 4,6-Dimethoxypyrimidin-2-yl group
Tri: 4,6-Dimethoxy-s-triazin-2-yl group
Ph: Phenyl group
(g): 2-(4,6-Dimethylpyrimidin-2-yl)thio group
(h): 2-(4-Methoxy-6-methyl-s-triazin-2-yl)thio group
(i): 2-(4-Methoxy-6-methylpyrimidin-2-yl)thio group
(m): 2-(4-Chloro-6-methoxypyrimidin-2-yl)thio group Also, examples of the intermediate products as prepared above, are given in the following Table 2 and Table 3.

TABLE 1

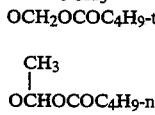

| Compound No. | R | $X^1$, $X^2$ | A | Physical properties Melting point (°C.) or Refractive index ($n_D^{20}$) |
|---|---|---|---|---|
| 1 | OH | 4-Ph | 2-S—Pym | 191-195 |
| 2 | OCH$_3$ | 4-Ph | 2-S—Pym | 115~117 |
| 3 | OCH$_2$OCOC$_4$H$_9$-t | 4-Ph | 2-S—Pym | 1.5712 |
| 4 | OCH(CH$_3$)COC$_4$H$_9$-n | 4-Ph | 2-S—Pym | 1.5670 |
| 5 | OH | 4-Ph, 6-CH$_3$ | 2-S—Pym | 154~159 |
| 6 | OH | 4-(4-CH$_3$-phenyl) | 2-S—Pym | 179~183.5 |
| 7 | OCH$_3$ | 4-(4-CH$_3$-phenyl) | 2-S—Pym | 149~151 |
| 8 | OCH$_3$ | 4-(4-Cl-phenyl) | 2-S—Pym | 138~141.5 |
| 9 | OH | 4-(4-Cl-phenyl) | 2-S—Pym | 219~223 |
| 10 | OCH$_3$ | 4-(2-Cl-phenyl) | 2-S—Pym | 1.6042 |
| 11 | OH | 4-(2-Cl-phenyl) | 2-S—Pym | 181~184 |

TABLE 1-continued

Structure: X¹ and X² on positions 5,6 of a ring with N at position 1, A substituent at position 1, position 2 double bond, position 3 bearing COR, position 4.

| Compound No. | R | X¹, X² | A | Physical properties Melting point (°C.) or Refractive index ($n_D^{20}$) |
|---|---|---|---|---|
| 12 | OCH₃ | 4-phenyl with 2-CH₃, CH₃ | 2-S—Pym | 1.5961 |
| 13 | OH | 4-phenyl with 2-CH₃, CH₃ | 2-S—Pym | 95~99 |
| 14 | OCH₃ | 4-phenyl-F | 2-S—Pym | 151~154 |
| 15 | OH | 4-phenyl-F | 2-S—Pym | 193-197 |
| 16 | OCH₃ | 4-phenyl-F, 6-CH₃ | 2-S—Pym | 120~123 |
| 17 | OH | 4-phenyl-F, 6-CH₃ | 2-S—Pym | 155.5~158 |
| 18 | OCH₂OCOC₄H₉-t | 4-phenyl with 2-CH₃, CH₃ | 2-S—Pym | 1.5640 |
| 19 | OCH₂OCOC₄H₉-t | 4-phenyl-F | 2-S—Pym | 1.5615 |
| 20 | OCH₂OCOC₄H₉-t | 4-phenyl-F, 6-CH₃ | 2-S—Pym | 1.5619 |
| 21 | OCH₃ | 4-phenyl-Br | 2-S—Pym | 134~137.5 |
| 22 | OH | 4-phenyl-Br | 2-S—Pym | 178-181 |

TABLE 1-continued

Structure:
- Position 4: COR
- Positions 5,6: X¹, X²
- Position 1: A
- N at position 1-adjacent

| Compound No. | R | X¹, X² | A | Physical properties Melting point (°C.) or Refractive index ($n_D^{20}$) |
|---|---|---|---|---|
| 23 | OCH₃ | 4-, 3-Cl, 4-Cl phenyl | 2-S—Pym | 135~139 |
| 24 | OH | 4-, 3-Cl, 4-Cl phenyl | 2-S—Pym | 169~172 |
| 25 | OCH₃ | 4-C₂H₅ phenyl | 2-S—Pym | 90.5~94 |
| 26 | OH | 4-C₂H₅ phenyl | 2-S—Pym | 178~180 |
| 27 | OCH₂OCOC₄H₉-t | 4-, 3-Cl, 4-Cl phenyl | 2-S—Pym | 1.5796 |
| 28 | OCH₂OCOC₄H₉-t | 4-C₂H₅ phenyl | 2-S—Pym | 1.5687 |
| 29 | OCH₃ | 4-, 3-CH₃, 4-Cl phenyl | 2-S—Pym | 74~78 |
| 30 | OH | 4-, 3-CH₃, 4-Cl phenyl | 2-S—Pym | 170.5~174 |
| 31 | OCH₃ | 4-NO₂ phenyl | 2-S—Pym | unmeasurable |
| 32 | OH | 4-NO₂ phenyl | 2-S—Pym | 160~162 |
| 33 | OCH₃ | 4-CF₃ phenyl | 2-S—Pym | 1.5681 |

TABLE 1-continued structure: pyridine ring with positions 1(N)-A, 2, 3-COR, 4, 5-X¹, 6-X²

| Compound No. | R | X¹, X² | A | Physical properties Melting point (°C.) or Refractive index ($n_D^{20}$) |
|---|---|---|---|---|
| 34 | OH | 4-(4-CF₃-phenyl) | 2-S—Pym | 179~182 |
| 35 | OCH₃ | 4-(4-i-C₃H₇-phenyl) | 2-S—Pym | 1.5786 |
| 36 | OH | 4-(4-i-C₃H₇-phenyl) | 2-S—Pym | 173~176 |
| 37 | OCH₃ | 4-Ph, 5-CH₃ | 2-S—Pym | 150~153 |
| 38 | OH | 4-Ph, 5-CH₃ | 2-S—Pym | 140~143 |
| 39 | OCH₂OCOC₄H₉-t | 4-(4-CF₃-phenyl) | 2-S—Pym | 1.5409 |
| 40 | OCH₂OCOC₄H₉-t | 4-(4-i-C₃H₇-phenyl) | 2-S—Pym | 1.5641 |
| 41 | OCH₃ | 4-(4-F-phenyl) | 2-S—Pym | 117~120 |
| 42 | OH | 4-(4-F-phenyl) | 2-S—Pym | 199.5~202 |
| 43 | OCH₃ | 4-(4-OCH₃-phenyl) | 2-S—Pym | 107~110 |
| 44 | OH | 4-(4-OCH₃-phenyl) | 2-S—Pym | 198~201 |
| 45 | OCH₂OCOC₄H₉-t | 4-(4-F-phenyl) | 2-S—Pym | 1.5659 |
| 46 | OCH₃ | 4-(4-CH₃-phenyl) | 2-S—Pym | 1.5990 |

TABLE 1-continued

[Structure: ring with positions 1-6, N at position 1, A substituent at position 1, COR at position 3, X¹ at position 5, X² at position 6]

| Compound No. | R | X¹, X² | A | Physical properties Melting point (°C.) or Refractive index ($n_D^{20}$) |
|---|---|---|---|---|
| 47 | OH | 4-(4-CH₃-phenyl) | 2-S—Pym | 182~184 |
| 48 | OCH₂OCOC₄H₉-t | 4-(4-CH₃-phenyl) | 2-S—Pym | 1.5625 |
| 49 | OCH₃ | 4-(3,4-diF-phenyl) | 2-S—Pym | 118~121 |
| 50 | OH | 4-(3,4-diF-phenyl) | 2-S—Pym | 185~187 |
| 51 | OCH₃ | 4-(3-Cl-phenyl) | 2-S—Pym | 1.6074 |
| 52 | OH | 4-(3-Cl-phenyl) | 2-S—Pym | 187~190 |
| 53 | OCH₃ | 4-Ph, 5-C₂H₅ | 2-S—Pym | 143.5~146 |
| 54 | OH | 4-Ph, 5-C₂H₅ | 2-S—Pym | 163~166.5 |
| 55 | OH | 4-Ph, 5-OCH₃ | 2-S—Pym | 157~162 |
| 56 | OH | 4-(4-C₃H₇-phenyl) | 2-S—Pym | 156.5~160 |
| 57 | OCH₂OCOC₄H₉-t | 4-(4-C₃H₇-phenyl) | 2-S—Pym | 1.5719 |
| 58 | OCH₂OCOC₄H₉-t | 4-(3-Cl-phenyl) | 2-S—Pym | 1.5719 |
| 59 | OH | 4-(4-piperidinyl-phenyl) | 2-S—Pym | 188~192 |

TABLE 1-continued
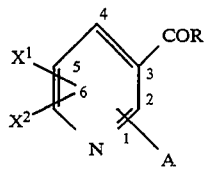
| Compound No. | R | X¹, X² | A | Physical properties Melting point (°C.) or Refractive index ($n_D^{20}$) |
|---|---|---|---|---|
| 60 | OCH₃ | 4-—⟨⟩—OC₂H₅ | 2-S—Pym | 96~100 |
| 61 | OH | 4-—⟨⟩—OC₂H₅ | 2-S—Pym | 178~181 |
| 62 | OCH₃ | 4-—⟨⟩—OC₃H₇ | 2-S—Pym | 1.5976 |
| 63 | OH | 4-—⟨⟩—OC₃H₇ | 2-S—Pym | 172.5~174.5 |
| 64 | OCH₃ | 4-—⟨⟩(—OCH₃, —OCH₃) | 2-S—Pym | 146~148 |
| 65 | OH | 4-—⟨⟩(—OCH₃, —OCH₃) | 2-S—Pym | 184.5~187 |
| 66 | OCH₃ | 4-—⟨⟩—Br | 2-S—Pym | 1.6091 |
| 67 | OH | 4-—⟨⟩—Br | 2-S—Pym | 174~176 |
| 68 | OCH₃ | 4-—⟨⟩—CH₃ | 2-S—Pym | 125~127 |
| 69 | OH | 4-—⟨⟩—CH₃ | 2-S—Pym | 201~203.5 |
| 70 | OCH₃ | 4-—⟨⟩—F | 2-S—Pym | 1.5907 |

TABLE 1-continued

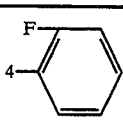

| Compound No. | R | X¹, X² | A | Physical properties Melting point (°C.) or Refractive index ($n_D^{20}$) |
|---|---|---|---|---|
| 71 | OH | 4-F-Ph | 2-S—Pym | 170~172 |
| 72 | OCH₃ | 4-(OC₃H₇-i)-Ph | 2-S—Pym | 1.5831 |
| 73 | OH | 4-(OC₃H₇-i)-Ph | 2-S—Pym | 177~179 |
| 74 | OCH₃ | 4-(OC₃H₇-i)-Ph | (g) | 1.5965 |
| 75 | OH | 4-(OC₃H₇-i)-Ph | (g) | 172~174 |
| 76 | OCH₃ | 4-Ph | (h) | |
| 77 | OH | 4-Ph | (h) | 125~128 |
| 78 | OCH₃ | 4-Ph | (g) | |
| 79 | OH | 4-Ph | (g) | 145~150 |
| 80 | OCH₂OCOC₄H₉ | 4-Ph | 2-S—Tri | 1.5562 |
| 81 | OCH₃OCOC₄H₉-t | 4-Ph | 2-S—Tri | unmeasurable |
| 82 | OCH₃ | 4-O—Ph | 2-S—Pym | |
| 83 | OH | 4-O—Ph | 2-S—Pym | |
| 84 | OCH₂OCOC₄H₉-t | 4-O—Ph | 2-S—Pym | |
| 85 | OCH₃ | 4-S—Ph | 2-S—Pym | |
| 86 | OH | 4-S—Ph | 2-S—Pym | |
| 87 | OCH₂OCOC₄H₉-t | 4-S—Ph | 2-S—Pym | |
| 88 | OCH₃ | 2-Cl, 4-S-Ph | 2-S—Pym | |
| 89 | OH | 2-Cl, 4-S-Ph | 2-S—Pym | |
| 90 | OCH₂OCOC₄H₉-t | 2-Cl, 4-S-Ph | 2-S—Pym | |
| 91 | OCH₃ | 3-Cl, 4-S-Ph | 2-S—Pym | |

TABLE 1-continued
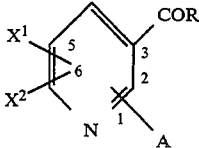
| Compound No. | R | X¹, X² | A | Physical properties Melting point (°C.) or Refractive index ($n_D^{20}$) |
|---|---|---|---|---|
| 92 | OH | 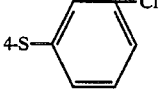 4-S, Cl | 2-S—Pym | |
| 93 | OCH₂OCOC₄H₉-t | 4-S, Cl | 2-S—Pym | |
| 94 | OCH₃ | 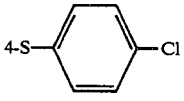 4-S, 4-Cl | 2-S—Pym | |
| 95 | OH | 4-S, 4-Cl | 2-S—Pym | |
| 96 | OCH₂OCOC₄H₉-t | 4-S, 4-Cl | 2-S—Pym | |
| 97 | OCH₃ |  Cl, 4-O | 2-S—Pym | |
| 98 | OH | Cl, 4-O | 2-S—Pym | |
| 99 | OCH₂OCOC₄H₉-t | Cl, 4-O | 2-S—Pym | |
| 100 | OCH₃ | 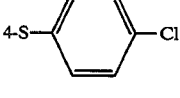 4-O, Cl | 2-S—Pym | |
| 101 | OH | 4-O, Cl | 2-S—Pym | |
| 102 | OCH₂OCOC₄H₉-t | 4-O, Cl | 2-S—Pym | |

TABLE 1-continued $$\text{structure with } X^1 \text{ at position 5, } X^2 \text{ at position 6, N at position 1, A at position 1, COR at position 3}$$

| Compound No. | R | $X^1, X^2$ | A | Physical properties Melting point (°C.) or Refractive index ($n_D^{20}$) |
|---|---|---|---|---|
| 103 | OCH$_3$ | 4-O—C$_6$H$_4$—Cl | 2-S—Pym | |
| 104 | OH | 4-O—C$_6$H$_4$—Cl | 2-S—Pym | |
| 105 | OCH$_2$OCOC$_4$H$_9$-t | 4-O—C$_6$H$_4$—Cl | 2-S—Pym | |
| 106 | OCH$_3$ | 4-S—C$_6$H$_4$(2-CH$_3$) | 2-S—Pym | |
| 107 | OH | 4-S—C$_6$H$_4$(2-CH$_3$) | 2-S—Pym | |
| 108 | OCH$_2$OCOC$_4$H$_9$-t | 4-S—C$_6$H$_4$(2-Cl) | 2-S—Pym | |
| 109 | OCH$_3$ | 4-S—C$_6$H$_4$(3-CH$_3$) | 2-S—Pym | |
| 110 | OH | 4-S—C$_6$H$_4$(3-CH$_3$) | 2-S—Pym | |
| 111 | OCH$_2$OCOC$_4$H$_9$-t | 4-S—C$_6$H$_4$(3-CH$_3$) | 2-S—Pym | |
| 112 | OCH$_3$ | 4-S—C$_6$H$_4$(4-CH$_3$) | 2-S—Pym | |
| 113 | OH | 4-S—C$_6$H$_4$(4-CH$_3$) | 2-S—Pym | |

TABLE 1-continued

| Compound No. | R | X¹, X² | A | Physical properties Melting point (°C.) or Refractive index ($n_D^{20}$) |
|---|---|---|---|---|
| 114 | OCH$_2$OCOC$_4$H$_9$-t | 4-S—C$_6$H$_4$—CH$_3$ | 2-S—Pym | |
| 115 | OCH$_3$ | 4-S, 2-OCH$_3$-phenyl | 2-S—Pym | |
| 116 | OH | 4-S, 2-OCH$_3$-phenyl | 2-S—Pym | |
| 117 | OCH$_2$OCOC$_4$H$_9$-t | 4-S, 2-OCH$_3$-phenyl | 2-S—Pym | |
| 118 | OCH$_3$ | 4-S, 3-OCH$_3$-phenyl | 2-S—Pym | |
| 119 | OH | 4-S, 3-OCH$_3$-phenyl | 2-S—Pym | |
| 120 | OCH$_2$OCOC$_4$H$_9$-t | 4-S, 3-OCH$_3$-phenyl | 2-S—Pym | |
| 121 | OCH$_3$ | 4-S, 4-OCH$_3$-phenyl | 2-S—Pym | |
| 122 | OH | 4-S, 4-OCH$_3$-phenyl | 2-S—Pym | |
| 123 | OCH$_2$OCOC$_4$H$_9$-t | 4-S, 4-OCH$_3$-phenyl | 2-S—Pym | |
| 124 | OH | 4-COCH$_3$ | 2-S—Pym | |
| 125 | OH | 4-C(CH$_3$)=NOCH$_3$ | 2-S—Pym | |

TABLE 1-continued

| Compound No. | R | X¹, X² | A | Physical properties Melting point (°C.) or Refractive index ($n_D^{20}$) |
|---|---|---|---|---|
| 126 | OH | 4-O-phenyl with CH₃ at 2-position | 2-S—Pym | |
| 127 | OH | 4-O-phenyl with CH₃ at 3-position | 2-S—Pym | |
| 128 | OH | 4-O-phenyl with CH₃ at 4-position | 2-S—Pym | |
| 129 | OH | 4-O-phenyl with CH₃O at 2-position | 2-S—Pym | |
| 130 | OH | 4-O-phenyl with OCH₃ at 3-position | 2-S—Pym | |
| 131 | OH | 4-O-phenyl with OCH₃ at 4-position | 2-S—Pym | |
| 132 | OH | 4-NH—Ph | 2-S—Pym | |
| 133 | OH | 4-CH₂—Ph | 2-S—Pym | |
| 134 | OH | 4-phenyl with Br and N(CH₃)₂ | 2-S—Pym | |
| 135 | OH | 4-phenyl with CH₃ and N(CH₃)₂ | 2-S—Pym | |
| 136 | OH | 4-phenyl with Cl and N(CH₃)₂ | 2-S—Pym | |
| 137 | OH | 4-COC₂H₅ | 2-S—Pym | |
| 138 | OH | 4-C(C₂H₅)=N—OCH₃ | 2-S—Pym | |
| 139 | OH | 4-C(CH₃)=N—OC₂H₅ | 2-S—Pym | |

TABLE 1-continued

[Structure: 6-membered ring with N at position 1, positions numbered 1-6, with substituent A at position 1, COR at position 3 (with double bond between 3 and 4), X¹ at position 5, X² at position 6]

| Compound No. | R | $X^1, X^2$ | A | Physical properties Melting point (°C.) or Refractive index ($n_D^{20}$) |
|---|---|---|---|---|
| 140 | OH | 4-CH=N—OCH₃ | 2-S—Pym | |
| 141 | OH | 4-CH₃—(C₆H₃)—Cl | 2-S—Pym | |
| 142 | OH | 4-COOH | 2-S—Pym | |
| 143 | OCH₃ | 4-COOCH₃ | 2-S—Pym | |
| 144 | OH | 4-COOCH₃ | 2-S—Pym | |
| 145 | SCH₃ | 4-Ph | 2-S—Pym | |
| 146 | H | 4-Ph | 2-S—Pym | |
| 147 | OH | 2-Ph | 2-S—Pym | |
| 148 | OH | 2-(C₆H₄)—Cl | 2-S—Pym | |
| 149 | OH | 4-(C₆H₄)—SCH₃ | 2-S—Pym | |
| 150 | OH | 4-(C₆H₄)—SCH₃ (ortho SCH₃) | 2-S—Pym | |
| 151 | OH | 4-(C₆H₄) with CH₃S- (ortho) | 2-S—Pym | |
| 152 | OH | 4-SCH₃ | 2-S—Pym | |
| 153 | OH | 4-NH—(C₆H₄)—Cl | 2-S—Pym | |
| 154 | OH | 4-NH—(C₆H₄)—Cl (ortho Cl) | 2-S—Pym | |
| 155 | OH | 4-NH—(C₆H₄) with Cl (ortho) | 2-S—Pym | |
| 156 | OH | 4-SC₂H₅ | 2-S—Pym | |
| 157 | OH | 4-O—C(=N—OCH₃)—CH=C(—N—OCH₃) | 2-S—Pym | |

TABLE 1-continued

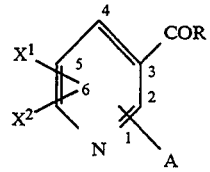

| Compound No. | R | X¹, X² | A | Physical properties Melting point (°C.) or Refractive index ($n_D^{20}$) |
|---|---|---|---|---|
| 158 | OCH₃ | 4-Ph | 2-S—Tri | |
| 159 | OH | 4-Ph | 2-S—Tri | 146~147.5 |
| 160 | OC₂H₅ | 4-[C₆H₄-Cl] | 2-S—Pym | 89~98 |
| 161 | NHSO₂CH₃ | 4-[C₆H₄-Cl (3-Cl)] | 2-S—Pym | 54~58 |
| 162 | 2,5-(OCH₃)₂-C₆H₃ | 4-[C₆H₄-Cl] | 2-S—Pym | 54~61 |
| 163 | 2-Cl-5-OCH₃-C₆H₃ | 4-[C₆H₄-Cl] | 2-S—Pym | unmeasurable |
| 164 | SCH₃ | 4-[C₆H₄-Cl] | 2-S—Pym | 131~132 |
| 165 | O—Ph | 4-[C₆H₄-Cl] | 2-S—Pym | unmeasurable |
| 166 | S—Ph | 4-[C₆H₄-Cl] | 2-S—Pym | |
| 167 | O⁻Na⁺ | 4-[C₆H₄-Cl] | 2-S—Pym | 244~247 |
| 168 | OCH(CH₃)—OCOC₄H₉-t | 4-[C₆H₄-Cl] | 2-S—Pym | |
| 169 | OCH₃ | 4-Ph | (i) | |
| 170 | OH | 4-Ph | (i) | 137~141 |
| 171 | OCH(CH₃)—OCOC₄H₉-t | 4-[C₆H₄-OCHF₂] | 2-S—Pym | |

TABLE 1-continued

Structure: pyridine-type ring with positions 1-6, where position 1 bears A, position 2 has substituent, position 3 bears COR, position 4 shown, positions 5 and 6 bear X¹ and X² respectively, with N in the ring.

| Compound No. | R | X¹, X² | A | Physical properties Melting point (°C.) or Refractive index ($n_D^{20}$) |
|---|---|---|---|---|
| 172 | OH | 4-(C₆H₄)-OCHF₂ | 2-S—Pym | |
| 173 | OCH₂OCOC₄H₉-t | 4-(C₆H₄)-N(CH₃)₂ | 2-S—Pym | |
| 174 | OH | 4-(C₆H₄)-N(CH₃)₂ | 2-S—Pym | 173~177 |
| 175 | OCH₃ | 4-(C₆H₄)-OCH₃ (ortho) | 2-S—Pym | 1.5938 |
| 176 | OH | 4-(C₆H₄)-OCH₃ (ortho) | 2-S—Pym | 189~192 |
| 177 | OCH₂OCOC₄H₉-t | 4-(C₆H₄)-OCH₃ (meta) | 2-S—Pym | |
| 178 | OH | 4-(C₆H₄)-OCH₃ (meta) | 2-S—Pym | 187.5~189 |
| 179 | OCHOCOC₄H₉-t (with CH₃) | 4-(C₆H₄)-OC₃H₇ | 2-S—Pym | |
| 180 | OH | 4-(C₆H₄)-OC₃H₇ | 2-S—Pym | |
| 181 | OCH₂OCOC₄H₉-t | 4-(C₆H₄)-OC₃H₇-i | 2-S—Pym | |
| 182 | OH | 4-(C₆H₄)-OC₃H₇-i | 2-S—Pym | |

TABLE 1-continued

Structure:
$X^1$ at position 5, $X^2$ at position 6, COR at position 3, A at position 1 (on N), with positions 2, 4 on ring.

| Compound No. | R | $X^1$, $X^2$ | A | Physical properties Melting point (°C.) or Refractive index ($n_D^{20}$) |
|---|---|---|---|---|
| 183 | OCH₂OCOC₄H₉-t | 4-(C₆H₄-O-Ph) | 2-S—Pym | |
| 184 | OH | 4-(C₆H₄-O-Ph) | 2-S—Pym | |
| 185 | OCH₃ | 4-(C₆H₄-O-C₆H₄-CH₃) | 2-S—Pym | |
| 186 | OH | 4-(C₆H₄-O-C₆H₄-CH₃) | 2-S—Pym | |
| 187 | OH | 4-(C₆H₄-OCH₂OCH₃) | 2-S—Pym | |
| 188 | OCH(CH₃)—OCOC₄H₉-t | 4-Ph, 5-Cl | 2-S—Pym | |
| 189 | OH | 4-Ph, 5-Cl | 2-S—Pym | |
| 190 | OCH₂OCOC₄H₉-t | 4-Ph, 5-N(CH₃)₂ | 2-S—Pym | |
| 191 | OH | 4-Ph, 5-N(CH₃)₂ | 2-S—Pym | |
| 192 | OCH₂OCOC₄H₉-t | 4-Ph, 6-Cl | 2-S—Pym | |
| 193 | OH | 4-Ph, 6-Cl | 2-S—Pym | |
| 194 | OCH₂OCOC₄H₉-t | 4-Ph, 6-OCH₃ | 2-S—Pym | |
| 195 | OH | 4-Ph, 6-OCH₃ | 2-S—Pym | |
| 196 | OCH(CH₃)—OCOC₄H₉-t | 4-Ph, 6-N(CH₃)₂ | 2-S—Pym | |
| 197 | OH | 4-Ph, 6-N(CH₃)₂ | 2-S—Pym | |
| 198 | OCH₂OCOC₄H₉-t | 4-Ph, 6-C₂H₅ | 2-S—Pym | |
| 199 | OH | 4-Ph, 6-C₂H₅ | 2-S—Pym | |

TABLE 1-continued

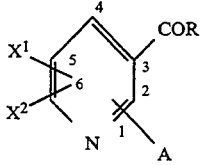

| Compound No. | R | X¹, X² | A | Physical properties Melting point (°C.) or Refractive index ($n_D^{20}$) |
|---|---|---|---|---|
| 200 | OH | 4- phenyl with OCHF$_2$ | 2-S—Pym | |
| 201 | OH | 4- phenyl with OC$_2$H$_5$ | 2-S—Pym | |
| 202 | OH | 4- phenyl with Cl, OCH$_3$ | 2-S—Pym | |
| 203 | OH | 4- phenyl with Br, OCH$_3$ | 2-S—Pym | |
| 204 | OH | 4- phenyl with CH$_3$, OCH$_3$ | 2-S—Pym | |
| 205 | OH | 4- phenyl with Cl, Cl | 2-S—Pym | |
| 206 | OH | 4- phenyl with Br, Br | 2-S—Pym | |
| 207 | OH | 4- phenyl with F, OCH$_3$ | 2-S—Pym | |
| 208 | OH | 4- phenyl with Cl, OCHF$_2$ | 2-S—Pym | |
| 209 | OH | 4- phenyl with CHF$_2$, OCHF$_2$ | 2-S—Pym | |
| 210 | OH | 4- phenyl with Cl, OCH$_3$, Cl | 2-S—Pym | |

TABLE 1-continued
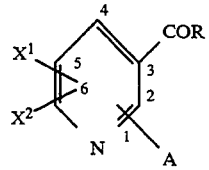
| Compound No. | R | X¹, X² | A | Physical properties Melting point (°C.) or Refractive index ($n_D^{20}$) |
|---|---|---|---|---|
| 211 | -N⌐⌐N (imidazolyl) | 4-C₆H₄-Cl | 2-S—Pym | 145.5~147 |
| 212 | OH | 4-C₆H₃(OCH₃)(Br) | 2-S—Pym | |
| 213 | OH | 4-C₆H₄-CN | 2-S—Pym | |
| 214 | OH | 4-C₆H₄-C≡CH | 2-S—Pym | |
| 215 | OH | 4-C₆H₄-NHCH₃ | 2-S—Pym | |
| 216 | OH | 4-C₆H₄-OCH₂COOC₂H₅ | 2-S—Pym | |
| 217 | OH | 4-C₆H₃(CH₃)-OCH(CH₃)COOC₂H₅ | 2-S—Pym | |
| 218 | OH | 4-C₆H₃(Br)(CH₂OCH₃) | 2-S—Pym | |
| 219 | OH | 4-C₆H₃(Br)(CH₂OCH₃) | 2-S—Pym | |
| 220 | OH | 4-C₆H₃(Br)(OCH₂CH₂OCH₃) | 2-S—Pym | |
| 221 | OH | 4-C₆H₃(Br)(OCH₂OC₂H₅) | 2-S—Pym | |

TABLE 1-continued

Structure: Pyridine ring with COR at position 3, X¹ at position 5, X² at position 6, and A at position 1 (N).

| Compound No. | R | X¹, X² | A | Physical properties Melting point (°C.) or Refractive index ($n_D^{20}$) |
|---|---|---|---|---|
| 222 | OH | 4-phenyl with 2-Br, 1-OCH₂SCH₃ | 2-S—Pym | |
| 223 | OH | 4-phenyl with 2-Br, 1-OCH₂COC₂H₅ | 2-S—Pym | |
| 224 | OH | 4-phenyl with OC₂H₅, OCH₃ | 2-S—Pym | |
| 225 | OH | 4-phenyl with NHC₃H₇, OCH₃ | 2-S—Pym | |
| 226 | OH | 4-phenyl with 2-Br, 1-OCH₂CH₂SCH₃ | 2-S—Pym | |
| 227 | OH | 4-phenyl with 2-Br, 1-OCH₂SC₂H₅ | 2-S—Pym | |
| 228 | OH | 4-phenyl with 2-Br, 1-OH | 2-S—Pym | |
| 229 | OH | 4-phenyl with 2-Br, 1-OCH₂—Ph | 2-S—Pym | |
| 230 | OCH₃ | 4-phenyl with OCH₃ | 2-S—Pym | 1.5901 |
| 231 | OH | 4-phenyl with OCH₂OC₂H₅ | 2-S—Pym | 135–138 |
| 232 | OH | 4-phenyl with OCH₂OC₂H₅ | 2-S—Pym | |

TABLE 1-continued

Structure:
- Position 4: COR
- Position 5: X¹
- Position 6: X²
- Position 1: N, A
- Positions 2, 3 on ring

| Compound No. | R | X¹, X² | A | Physical properties Melting point (°C.) or Refractive index ($n_D^{20}$) |
|---|---|---|---|---|
| 233 | O⁻N⁺H₃C₃H₇-i | 4-(C₆H₄)-Cl | 2-S—Pym | 161~168 |
| 234 | OH | 4-SCH₂—Ph | 2-S—Pym | 138~144 |
| 235 | OH | 4-OCHF₂ | 2-S—Pym | |
| 236 | OH | 4-Ph | (m) | 202~205 |
| 237 | OH | 4-OCH₂—Ph | 2-S—Pym | |
| 238 | OH | 4-OCH₂CH=CH₂ | 2-S—Pym | |
| 239 | OH | 4-OCH₂C≡CH | 2-S—Pym | |
| 240 | OH | 4-cyclopentyl | 2-S—Pym | |
| 241 | OH | 5-Ph | 2-S—Pym | |
| 242 | OH | 6-Ph | 2-S—Pym | |
| 243 | OCH₂OCO—Ph | 4-Ph | 2-S—Pym | |
| 244 | OH | 4-NHCO—Ph | 2-S—Pym | |
| 245 | OCH₃ | 4-SCH₂—Ph | 2-S—Pym | 81~86 |

TABLE 2

Structure:

$$(CH_3)_2N-C(R^5)=C(R^4)-C(R^3)=C(CN)(COOR^6)$$

| Intermediate No. | R³ | R⁴ | R⁵ | R⁶ | Physical properties Melting point (°C.) or Refractive index ($n_D^{20}$) |
|---|---|---|---|---|---|
| 1 | Ph— | H | H | CH₃ | 144~146 |
| 2 | Ph— | H | H | C₂H₅ | |
| 3 | 4-CH₃-C₆H₄— | H | H | CH₃ | |
| 4 | 4-Cl-C₆H₄— | H | H | CH₃ | |
| 5 | 4-CH₃O-C₆H₄— | H | H | CH₃ | 175~178 |
| 6 | 2-Cl-C₆H₄— | H | H | CH₃ | 164~166.5 |

TABLE 2-continued $$\begin{array}{c} CH_3 \\ \diagdown \\ N-C=C-C=C \\ \diagup \quad | \quad | \quad | \diagdown \\ CH_3 \quad R^5 \quad R^4 \; R^3 \quad COOR^6 \end{array} \begin{array}{c} CN \\ \\ \end{array}$$

| Intermediate No. | R³ | R⁴ | R⁵ | R⁶ | Physical properties Melting point (°C.) or Refractive index ($n_D^{20}$) |
|---|---|---|---|---|---|
| 7 | Cl—C₆H₄— | H | H | CH₃ | 156~159 |
| 8 | Ph— | CH₃ | H | CH₃ | |
| 9 | Ph— | H | CH₃ | CH₃ | 180~184 |
| 10 | CH₃O— | H | H | CH₃ | 125~128 |
| 11 | CH₃— | H | H | CH₃ | 88~93 |
| 12 | (CH₃)₂N— | H | H | CH₃ | 121~126 |
| 13 | CH₃NH— | H | H | CH₃ | |
| 14 | CH₃—C₆H₄— (4-) | H | CH₃ | CH₃ | |
| 15 | i-C₃H₇— | H | H | CH₃ | 123~126 |
| 16 | i-C₃H₇— | H | CH₃ | CH₃ | |
| 17 | CH₃—C₆H₄— | H | H | CH₃ | 136~140 |
| 18 | (CH₃)₂—C₆H₃— | H | H | CH₃ | 183.5~188 |
| 19 | F—C₆H₄— (4-) | H | H | CH₃ | 198.5~200.5 |
| 20 | F—C₆H₄— (3-) | H | H | CH₃ | 215~217.5 |
| 21 | F—C₆H₄— (2-) | H | H | CH₃ | 157~159 |
| 22 | CH₃O—C₆H₄— | H | H | CH₃ | 159~162 |
| 23 | CH₃O—C₆H₄— (2-) | H | H | CH₃ | 122~126 |

TABLE 2-continued $$\underset{CH_3}{\overset{CH_3}{N}}-\underset{R^5}{\overset{R^4}{C}}=\underset{}{\overset{R^3}{C}}-\underset{COOR^6}{\overset{CN}{C}}$$

| Intermediate No. | R³ | R⁴ | R⁵ | R⁶ | Physical properties Melting point (°C.) or Refractive index ($n_D^{20}$) |
|---|---|---|---|---|---|
| 24 | 3,4-(CH₃O)₂-C₆H₃- | H | H | CH₃ | 205~208 |
| 25 | 4-Br-C₆H₄- | H | H | CH₃ | 219~223 |
| 26 | 3-Br-C₆H₄- | H | H | CH₃ | 180~184 |
| 27 | 4-C₂H₅O-C₆H₄- | H | H | CH₃ | 148~150 |
| 28 | 3-C₂H₅O-C₆H₄- | H | H | CH₃ | |
| 29 | 4-C₃H₇O-C₆H₄- | H | H | CH₃ | 147~149 |
| 30 | 4-i-C₃H₇O-C₆H₄- | H | H | CH₃ | 154~157 |
| 31 | 3-i-C₃H₇O-C₆H₄- | H | H | CH₃ | |
| 32 | 4-CHF₂O-C₆H₄- | H | H | CH₃ | |
| 33 | 3-CHF₂O-C₆H₄- | H | H | CH₃ | |
| 34 | 4-(CH₃)₂N-C₆H₄- | H | H | CH₃ | |
| 35 | 3-(CH₃)₂N-C₆H₄- | H | H | CH₃ | |

TABLE 2-continued $$\text{(CH}_3\text{)}_2\text{N}-\underset{R^5}{\overset{R^4}{C}}=\underset{}{\overset{R^3}{C}}-C\underset{COOR^6}{\overset{CN}{\diagdown}}$$

| Intermediate No. | R³ | R⁴ | R⁵ | R⁶ | Physical properties Melting point (°C.) or Refractive index ($n_D^{20}$) |
|---|---|---|---|---|---|
| 36 | 4-(piperidin-1-yl)phenyl | H | H | CH₃ | 149~152 |
| 37 | 4-C₂H₅-C₆H₄– | H | H | CH₃ | 127~130 |
| 38 | 4-C₃H₇-C₆H₄– | H | H | CH₃ | 129~131 |
| 39 | 3,4-F₂-C₆H₃– | H | H | CH₃ | 232~233.5 |
| 40 | 4-i-C₃H₇-C₆H₄– | H | H | CH₃ | 184~187 |
| 41 | 3-i-C₃H₇-C₆H₄– | H | H | CH₃ | |
| 42 | 4-CF₃-C₆H₄– | H | H | CH₃ | 225~227 |
| 43 | 3-CF₃-C₆H₄– | H | H | CH₃ | |
| 44 | 3-NO₂-C₆H₄– | H | H | CH₃ | |
| 45 | 2-CH₃-C₆H₄– | H | H | CH₃ | 155.5~157 |
| 46 | 4-CH₃S-C₆H₄– | H | H | CH₃ | |
| 47 | Ph—O— | H | H | CH₃ | 195~198 |
| 48 | 3-CH₃-4-Cl-C₆H₃– | H | H | CH₃ | 183~185.5 |

TABLE 2-continued $$CH_3\text{-}N(CH_3)\text{-}C(R^5)=C(R^4)\text{-}C(R^3)=C(CN)(COOR^6)$$

| Intermediate No. | $R^3$ | $R^4$ | $R^5$ | $R^6$ | Physical properties Melting point (°C.) or Refractive index ($n_D^{20}$) |
|---|---|---|---|---|---|
| 49 | Ph— | $OCH_3$ | H | $CH_3$ | 154~158 |
| 50 | 4-Br-C$_6$H$_4$— | H | $CH_3$ | $CH_3$ | 198~201 |
| 51 | 4-C$_2$H$_5$-C$_6$H$_4$— | H | $CH_3$ | $CH_3$ | 131~136 |
| 52 | 4-F-C$_6$H$_4$— | H | $CH_3$ | $CH_3$ | 190~192.5 |

TABLE 3

Pyridine with $R^3$, $R^4$, $R^5$, $COOR^6$, L substituents

| Intermediate No. | $R^3$ | $R^4$ | $R^5$ | $R^6$ | L | Physical properties Melting point (°C.) or Refractive index ($n_D^{20}$) |
|---|---|---|---|---|---|---|
| 53 | Ph— | H | H | $CH_3$ | Br | |
| 54 | Ph— | H | H | H | Cl | 190~194 |
| 55 | Ph— | H | H | H | Br | 181~184 |
| 56 | 4-Cl-C$_6$H$_4$— | H | H | $CH_3$ | Br | 73~76 |
| 57 | 4-Cl-C$_6$H$_4$— | H | H | H | Br | 204~208 |
| 58 | 4-Cl-C$_6$H$_4$— | H | H | H | Cl | 209~212 |
| 59 | 3-Cl-C$_6$H$_4$— | H | H | $CH_3$ | Br | |
| 60 | 3-Cl-C$_6$H$_4$— | H | H | H | Br | 178~182 |

TABLE 3-continued $$\text{structure with } R^3, R^4, R^5, COOR^6, L, N$$

| Intermediate No. | R³ | R⁴ | R⁵ | R⁶ | L | Physical properties Melting point (°C.) or Refractive index ($n_D^{20}$) |
|---|---|---|---|---|---|---|
| 61 | 2-Cl-C₆H₄- | H | H | CH₃ | Br | |
| 62 | 2-Cl-C₆H₄- | H | H | H | Br | 183~186.5 |
| 63 | 4-CH₃-C₆H₄- | H | H | CH₃ | Cl | |
| 64 | 4-CH₃-C₆H₄- | H | H | H | Cl | 195~199 |
| 65 | 3-CH₃-C₆H₄- | H | H | CH₃ | Br | |
| 66 | 3-CH₃-C₆H₄- | H | H | H | Br | 180~182 |
| 67 | 2-CH₃-C₆H₄- | H | H | CH₃ | Br | 166~169 |
| 68 | 2-CH₃-C₆H₄- | H | H | H | Br | |
| 69 | 4-CH₃O-C₆H₄- | H | H | CH₃ | Br | 89~90.5 |
| 70 | 4-CH₃O-C₆H₄- | H | H | H | Br | 206~209 |
| 71 | 3-CH₃O-C₆H₄- | H | H | CH₃ | Br | |

TABLE 3-continued
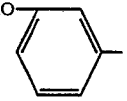
| Intermediate No. | R³ | R⁴ | R⁵ | R⁶ | L | Physical properties Melting point (°C.) or Refractive index (n_D^{20}) |
|---|---|---|---|---|---|---|
| 72 | CH₃O–C₆H₄– | H | H | H | Br | |
| 73 | 2-CH₃O-C₆H₄– | H | H | CH₃ | Br | |
| 74 | 2-CH₃O-C₆H₄– | H | H | H | Br | |
| 75 | 4-F-C₆H₄– | H | H | CH₃ | Br | 79~82 |
| 76 | 4-F-C₆H₄– | H | H | H | Br | |
| 77 | 3-F-C₆H₄– | H | H | CH₃ | Br | |
| 78 | 3-F-C₆H₄– | H | H | H | Br | 197~199.5 |
| 79 | 2-F-C₆H₄– | H | H | CH₃ | Br | 71~73 |
| 80 | 2-F-C₆H₄– | H | H | H | Br | 165~168.5 |
| 81 | 4-Br-C₆H₄– | H | H | CH₃ | Br | |
| 82 | 4-Br-C₆H₄– | H | H | H | Br | 215~219 |

TABLE 3-continued

Structure: pyridine ring with R³ and COOR⁶ on one carbon (with L substituent adjacent), R⁴, R⁵ on other positions, N in ring.

| Intermediate No. | R³ | R⁴ | R⁵ | R⁶ | L | Physical properties Melting point (°C.) or Refractive index ($n_D^{20}$) |
|---|---|---|---|---|---|---|
| 83 | Br—C₆H₄— | H | H | CH₃ | Br | 85.5~87 |
| 84 | Br—C₆H₄— | H | H | H | Br | 185~189 |
| 85 | C₂H₅O—C₆H₄— | H | H | CH₃ | Br | 83~84.5 |
| 86 | C₂H₅O—C₆H₄— | H | H | H | Br | 180~184 |
| 87 | C₂H₅O—C₆H₄— | H | H | CH₃ | Br | |
| 88 | C₂H₅O—C₆H₄— | H | H | H | Br | |
| 89 | C₃H₇O—C₆H₄— | H | H | CH₃ | Br | |
| 90 | C₃H₇O—C₆H₄— | H | H | H | Br | |
| 91 | C₃H₇O—C₆H₄— | H | H | CH₃ | Br | |
| 92 | C₃H₇O—C₆H₄— | H | H | H | Br | |
| 93 | i-C₃H₇O—C₆H₄— | H | H | CH₃ | Br | 168~173 |

TABLE 3-continued

Structure: pyridine ring with R³ and COOR⁶ at adjacent positions, R⁴, R⁵ on ring, L adjacent to N.

| Intermediate No. | R³ | R⁴ | R⁵ | R⁶ | L | Physical properties Melting point (°C.) or Refractive index ($n_D^{20}$) |
|---|---|---|---|---|---|---|
| 94 | 4-(i-$C_3H_7$O)-$C_6H_4$- | H | H | H | Br | 163~167 |
| 95 | 3-(i-$C_3H_7$O)-$C_6H_4$- | H | H | $CH_3$ | Br | |
| 96 | 3-(i-$C_3H_7$O)-$C_6H_4$- | H | H | H | Br | |
| 97 | 4-$C_2H_5$-$C_6H_4$- | H | H | $CH_3$ | Br | 73~75 |
| 98 | 4-$C_2H_5$-$C_6H_4$- | H | H | H | Br | 160~163 |
| 99 | 3-$C_2H_5$-$C_6H_4$- | H | H | $CH_3$ | Br | |
| 100 | 3-$C_2H_5$-$C_6H_4$- | H | H | H | Br | |
| 101 | 4-$C_3H_7$-$C_6H_4$- | H | H | H | Br | 69~73 |
| 102 | 4-$C_3H_7$-$C_6H_4$- | H | H | $CH_3$ | Br | |
| 103 | 3-$C_3H_7$-$C_6H_4$- | H | H | $CH_3$ | Br | |
| 104 | 3-$C_3H_7$-$C_6H_4$- | H | H | H | Br | |

TABLE 3-continued
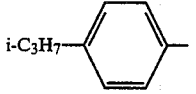
| Intermediate No. | R³ | R⁴ | R⁵ | R⁶ | L | Physical properties Melting point (°C.) or Refractive index ($n_D^{20}$) |
|---|---|---|---|---|---|---|
| 105 | 4-(i-C₃H₇)-C₆H₄- | H | H | CH₃ | Br | |
| 106 | 4-(i-C₃H₇)-C₆H₄- | H | H | H | Br | 173~176 |
| 107 | 3-(i-C₃H₇)-C₆H₄- | H | H | CH₃ | Br | |
| 108 | 3-(i-C₃H₇)-C₆H₄- | H | H | H | Br | |
| 109 | 4-NO₂-C₆H₄- | H | H | CH₃ | Br | |
| 110 | 4-NO₂-C₆H₄- | H | H | H | Br | 193~197 |
| 111 | 3-NO₂-C₆H₄- | H | H | CH₃ | Br | |
| 112 | 3-NO₂-C₆H₄- | H | H | H | Br | |
| 113 | 4-CF₃-C₆H₄- | H | H | CH₃ | Br | |
| 114 | 4-CF₃-C₆H₄- | H | H | H | Br | 188~191 |
| 115 | 3-CF₃-C₆H₄- | H | H | CH₃ | Br | |

TABLE 3-continued
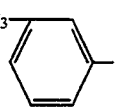
| Intermediate No. | R³ | R⁴ | R⁵ | R⁶ | L | Physical properties Melting point (°C.) or Refractive index ($n_D^{20}$) |
|---|---|---|---|---|---|---|
| 116 | 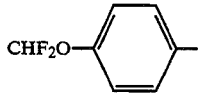 3-CF₃-C₆H₄ | H | H | H | Br | |
| 117 | 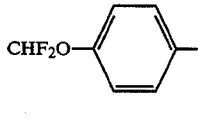 4-CHF₂O-C₆H₄ | H | H | CH₃ | Br | |
| 118 | 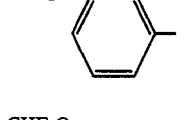 4-CHF₂O-C₆H₄ | H | H | H | Br | |
| 119 | 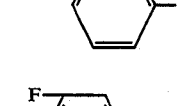 3-CHF₂O-C₆H₄ | H | H | CH₃ | Br | |
| 120 | 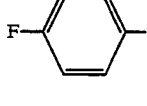 3-CHF₂O-C₆H₄ | H | H | H | Br | |
| 121 | 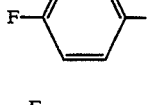 3,4-F₂-C₆H₃ | H | H | CH₃ | Br | 86~89 |
| 122 | 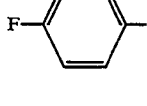 3,4-F₂-C₆H₃ | H | H | H | Br | 172~175 |
| 123 | 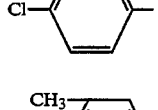 3,4-F₂-C₆H₃ | H | H | CH₃ | Br | 96~98 |
| 124 | 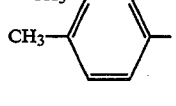 3,4-Cl₂-C₆H₃ | H | H | H | Br | 198~201 |
| 125 | 3,4-(CH₃)₂-C₆H₃ | H | H | CH₃ | Br | 89~92 |
| 126 | 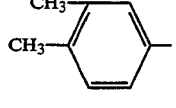 3,4-(CH₃)₂-C₆H₃ | H | H | H | Br | |

TABLE 3-continued

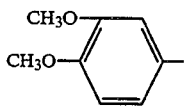

| Intermediate No. | R³ | R⁴ | R⁵ | R⁶ | L | Physical properties Melting point (°C.) or Refractive index ($n_D^{20}$) |
|---|---|---|---|---|---|---|
| 127 | 3,4-dimethoxyphenyl 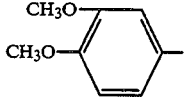 | H | H | $CH_3$ | Br | |
| 128 | 3,4-dimethoxyphenyl 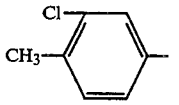 | H | H | H | Br | 208~210 |
| 129 | 3-chloro-4-methylphenyl 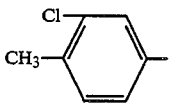 | H | H | $CH_3$ | Br | |
| 130 | 3-chloro-4-methylphenyl 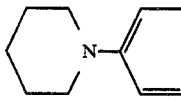 | H | H | H | Br | 174~177 |
| 131 | 4-piperidinophenyl 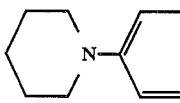 | H | H | $CH_3$ | Br | |
| 132 | 4-piperidinophenyl 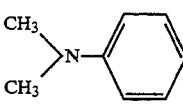 | H | H | H | Br | |
| 133 | 4-dimethylaminophenyl 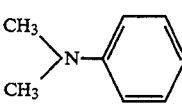 | H | H | $CH_3$ | Br | |
| 134 | 4-dimethylaminophenyl 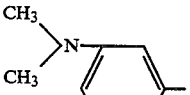 | H | H | H | Br | |
| 135 | 3-dimethylaminophenyl 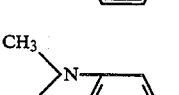 | H | H | $CH_3$ | Br | |
| 136 | 3-dimethylaminophenyl 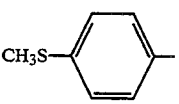 | H | H | H | Br | |
| 137 | 4-(methylthio)phenyl | H | H | $CH_3$ | Br | |

TABLE 3-continued

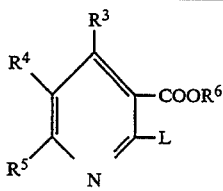

| Intermediate No. | R³ | R⁴ | R⁵ | R⁶ | L | Physical properties Melting point (°C.) or Refractive index (n_D²⁰) |
|---|---|---|---|---|---|---|
| 138 | CH₃S—C₆H₄— | H | H | H | Br | |
| 139 | CH₃S—C₆H₄— | H | H | CH₃ | Br | |
| 140 | CH₃S—C₆H₄— | H | H | H | Br | |
| 141 | Ph—O— | H | H | CH₃ | Br | 118~120 |
| 142 | Ph—O— | H | H | H | Br | |
| 143 | Ph— | CH₃ | H | CH₃ | Br | 129~133 |
| 144 | Ph— | CH₃ | H | H | Br | 216~218 |
| 145 | F—C₆H₄— | H | CH₃ | CH₃ | Br | 94~97 |
| 146 | F—C₆H₄— | H | CH₃ | H | Br | 199~201 |
| 147 | Ph— | C₂H₅ | H | CH₃ | Br | 129~132 |
| 148 | Ph— | C₂H₅ | H | H | Br | 173~175 |
| 149 | Ph— | CH₃O | H | CH₃ | Br | |
| 150 | Ph— | CH₃O | H | H | Br | 195~199 |
| 151 | i-C₃H₇— | H | H | CH₃ | Cl | |
| 152 | i-C₃H₇— | H | H | H | Cl | 156~158 |
| 153 | Ph— | H | CH₃ | CH₃ | Br | |
| 154 | Ph— | H | CH₃ | H | Br | |
| 155 | Ph—CH₃S— | H | H | H | Br | 165~169 |

The herbicidal composition of the present invention comprises at least one of the pyridine derivative of the general formula (I) and its salt as an effective ingredient.

The compound of the present invention can be used as it is as a herbicide, but it may be used in such an appropriate formulation as a dust, a wettable powder, an emulsifiable concentrate, a micro-particle agent or a granule agent by blending with a carrier, a surfactant, a dispersing agent or an adjuvant which may be generally used in the formulation of agricultural chemicals.

As a carrier to be used for these formulations, there may be enumerated a solid carrier such as Jeeklite, talc, bentonite, clay, kaolin, diatomaceous earth, white carbon, vemiculite, calcium carbonate, slaked lime, silica sand, ammonium sulfate or urea, or a liquid carrier such as isopropanol, xylene, cyclohexanone or methyl naphthalene.

As a surfactant and a dispersing agent, there may be enumerated, for example, a metal salt of an alkylbenzenesulfonic acid, a metal salt of a dinaphthylmethanedisulfonic acid, an alcohol-sulfuric acid ester, an alkylaryl sulfonate, a lignin sulfonate, a polyoxyethylene glycol ether, a polyoxyethylene alkyl aryl ether or a polyoxyethylene sorbitol monoalkylate. As an adjuvant, for example, carboxymethyl cellulose, polyethylene glycol or gum arabic may be enumerated.

The dust is prepared by blending the active ingredient with a powdery solid carrier. The wettable powder can be prepared by blending the active ingredient with a powdery solid carrier, a surfactant and a dispersing agent. The emulsifiable concentrate can be prepared by mixing the active ingredient with a liquid carrier, a surfactant and a dispersing agent. The granule agent can be prepared by coating a granular solid carrier with the active ingredient, together with an adjuvant, or by adding water to a solid carrier, the active ingredient and an adjuvant and extruding the mixture through apertures. The proportion of the active ingredient is optionally selected depending on its use, and it is usually from 0.01 to 20% by weight, preferably from 0.1 to 10% by weight, in the cases of dust and granule formulations, and from 0.1 to 80% by weight, preferably from 1 to 50% by weight, in the cases of emulsifiable concentrate and wettable powder formulations.

In practical use, the herbicide of the present invention may be diluted to a suitable concentration before applying or may be directly applied. The amount of the herbicide of the present invention may be optionally varied depending on the type of the compound used, the type of weed to be controlled, growing tendency, environmental conditions and the type of formulation used. When the herbicide of the present invention is directly applied as in the case of powder and granule formulation, it is used at a dose of from 0.1 g to 5 kg, preferably from 1 g to 1 kg of the active ingredient per 10 ares. In the case of liquid application such as emulsifiable concentrate and wettable powder formulations, the active ingredient may optionally be diluted to a concentration of from 0.1 to 10,000 ppm, preferably from 10 to 5,000 ppm for application.

The herbicide of the present invention may be applied to foliage, soil or water surface.

If desired, the compound of the present invention may be used in combination with insecticides, sterilizers, other herbicides, plant growth controlling agents, fertilizers or the like.

Now, typical Formulation Examples for the herbicidal composition of the present invention will be given. The types of compounds and additives and the blending ratios should not be limited thereto, and may optionally be varied in a wide range. In these Examples, "part" means "part by weight".

FORMULATION EXAMPLE 1 (wettable powder)

10 Parts of Compound No. 1, 0.5 part of polyoxyethyleneoctylphenyl ether, 0.5 part of sodium β-naphthalenesulfonate-formalin condensate, 20 parts of diatomaceous earth and 69 parts of clay were mixed and pulverized to obtain a wettable powder.

FORMULATION EXAMPLE 2 (wettable powder)

10 Parts of Compound No. 178, 0.5 part of Polyoxyethyleneoctylphenyl ether, 0.5 part of sodium β-naphthalenesulfonate-formalin condensate, 20 parts of diatomaceous earth, 5 parts of white carbon and 64 parts of clay were mixed and pulverized to obtain a wettable powder.

FORMULATION EXAMPLE 3 (wettable powder containing calcium carbonate)

10 Parts of Compound No. 22, 0.5 part of polyoxyethyleneoctylphenyl ether, 0.5 part of sodium naphthalenesulfonate-formalin condensate, 20 parts of diatomaceous earth, 5 parts of white carbon and 64 parts of calcium carbonate were mixed and pulverized to obtain a wettable powder.

FORMULATION EXAMPLE 4 (emulsifiable concentrate)

30 Parts of Compound No. 9, 60 parts of equivalent amount mixture of xylene and isophorone, and 10 parts of a surfactant mixture of polyoxyethylene sorbitol alkylate, polyoxyethylenealkylaryl polymer and alkylaryl sulfonate were fully stirred to obtain an emulsifiable concentrate.

FORMULATION EXAMPLE 5 (granule)

10 Parts of Compound No. 50, 80 parts of a bulking agent comprising a 1:3 mixture of talc and bentonite, 5 parts of white carbon, 5 parts of a surfactant mixture of polyoxyethylenesorbitol alkylate, polyoxyethylenealkylaryl polymer and alkylarylsulfonate and 10 parts of water were fully kneaded to obtain a paste-like material. The paste-like material was then extruded through a sieve aperture of 0.7 mm in diameter, and the extruded product was dried and cut into pieces of 0.5 to 1 mm in length to obtain granules.

The compound having the general formula (I) and its salt of the present invention are effective at a very small dosage for killing various troublesome weeds grown in upland fields in a wide range from germinating stage to growing stage, examples of the weeds including broadleaf weeds such as pale smartweed (*Polygonum lapathifolium*), slender amaranth (*Amaranthus viridis*), common lambsquarters (*Chenopodium album*), chickweed (*Stellaria media*), velvet leaf (*Abutilon theophrasti*), prickly sida (*Sida spinosa*), morningglory (Ipomoea sp.) and common cocklebur (*Xanthum strumarium*); perennial and annual cyperaceous weeds such as purple nutsedge (*Cyperus rotundus*), yellow nutsedge, *Cyperus esculetus*, umbrella plant (*Cyperus microiria*) and rice flatsedge (*Cyperus iria.*); and gramineous weeds such as barnyardgrass (*Echinochloa crus-galli*), crabgrass (Digitaria sp.), foxtail (Setaria sp.), annual bluegrass (*Poa annua*), johnsongrass (*Sorghum halepense*), *Alopecurus aequalis* and wild oats. Also, the compound of the present invention achieves excellent herbicidal effects on annual weeds such as barnyardgrass (*Echinochloa crusqalli*), small flower flatsedge (*Cyperus difformis*) and monochoria (*Monochoria vaginalis*), and perennial weeds such as *Sagittaria pygmaea, Cyperus serotinus, Eleocharis kuroguwai,* bulrush (*Scirpus hotarui*) and *Alisma canaliculatum,* grown in paddy fields. Depending on the type, the compound of the present invention does not have phytotoxicity to rice, wheat, cotton and corn, and is therefore suitable as a herbicide for cultivating these crops.

Now, the herbicidal effects of the compounds of the present invention will be described with reference to the following Test Examples.

TEST EXAMPLE 1

(Herbicidal effect test by paddy field soil treatment)

In a plastic pot (surface area: 100 cm$^2$) filled with paddy field soil, barnyardgrass (Ec), monochoria (Mo) and bulrush (Sc) were sown after puddling and leveling, and flooded to a water depth of 3 cm. Next day, a wettable powder prepared in accordance with Formulation Example 1 was diluted with water, and was applied dropwise to the water surface in such manner as to apply 100 g of the active ingredient per 10 ares. The plants were then cultured in a green house, and the evaluation of the herbicidal effect was conducted on the 21st day after the treatment in accordance with the standards as identified in Table 4. The results are shown in the following Table 5.

In the Test Examples, the following compounds were used as Comparative Examples. (Hereinafter, the same in each test.)

Comparative Compound A methyl 5-chloro-3-(4,6-dimethoxypyrimidin-2-yl)oxypicolinate (see Japanese Unexamined Patent Publication No. 84/1989)

Comparative Compound B

N-[3-(4,6-dimethoxypyrimidin-2yl)]trifluoromethanesulfonamide (see Japanese Unexamined Patent Publication No. 149567/1990)

Comparative Compound C 4-i-propyl-2-(4,6-dimethoxypyrimidin-2-yl)thionicotinic acid (see EP 467139)

Comparative Compound D methyl 5-chloro-2-(4,6-dimethoxypyrimidin-2-yl)thionicotinate (see EP 467139)

Comparative Compound E 5-chloro-2-(4,6-dimethoxypyrimidin-2-yl)thionicotinic acid (see EP 467139)

TABLE 4

| Index No. | Herbicidal effects and phytotoxicity (growing-controlling degree) |
|---|---|
| 5 | Herbicidal effect: at least 90% |
|   | Phytotoxicity: at least 90% |
| 4 | Herbicidal effect: at least 70% and less than 90% |
|   | Phytotoxicity: at least 70% and less than 90% |
| 3 | Herbicidal effect: at least 50% and less than 70% |
|   | Phytotoxicity: at least 50% and less than 70% |
| 2 | Herbicidal effect: at least 30% and less than 50% |
|   | Phytotoxicity: at least 30% and less than 50% |
| 1 | Herbicidal effect: at least 10% and less than 30% |
|   | Phytotoxicity: at least 10% and less than 30% |
| 0 | Herbicidal effect: 0 to less than 10% |
|   | Phytotoxicity: 0 to less than 10% |

TABLE 5

| Compound No. | Ec | Mo | Sc |
|---|---|---|---|
| 1 | 5 | 5 | 5 |
| 3 | 5 | 5 | 5 |
| 4 | 5 | 5 | 5 |
| 5 | 5 | 5 | 5 |
| 6 | 5 | 5 | 5 |
| 9 | 5 | 5 | 5 |
| 13 | 5 | 5 | 5 |
| 15 | 5 | 5 | 5 |
| 17 | 5 | 5 | 5 |
| 18 | 5 | 5 | 5 |
| 19 | 5 | 5 | 5 |
| 20 | 5 | 5 | 5 |
| 22 | 5 | 5 | 5 |
| 26 | 5 | 5 | 5 |
| 28 | 5 | 5 | 5 |
| 30 | 5 | 5 | 5 |
| 32 | 5 | 5 | 5 |
| 34 | 5 | 5 | 4 |
| 36 | 5 | 5 | 5 |
| 39 | 5 | 5 | 4 |
| 40 | 5 | 5 | 5 |
| 42 | 5 | 5 | 5 |
| 44 | 5 | 5 | 5 |
| 45 | 5 | 5 | 5 |
| 47 | 5 | 5 | 5 |
| 48 | 5 | 5 | 5 |
| 50 | 5 | 5 | 3 |
| 52 | 5 | 5 | 5 |
| 56 | 5 | 5 | 5 |
| 57 | 5 | 5 | 5 |
| 58 | 5 | 5 | 5 |
| 61 | 5 | 5 | 5 |
| 63 | 5 | 5 | 3 |

TABLE 5-continued

| Compound No. | Ec | Mo | Sc |
|---|---|---|---|
| 66 | 5 | 5 | 4 |
| 67 | 5 | 5 | 5 |
| 71 | 5 | 5 | 5 |
| 73 | 5 | 5 | 3 |
| 74 | 4 | 5 | 5 |
| 162 | 5 | 5 | 5 |
| 167 | 5 | 5 | 5 |
| 176 | 5 | 5 | 5 |
| 178 | 5 | 5 | 5 |
| 211 | 5 | 5 | 5 |
| 233 | 5 | 5 | 5 |
| (A) | 2 | 3 | 1 |
| (B) | 4 | 2 | 3 |
| (C) | 0 | 0 | 0 |
| (D) | 0 | 4 | 3 |
| (E) | 0 | 1 | 0 |

TEST EXAMPLE 2

(Herbicidal effect test by upland field soil treatment)

In a plastic pot (surface area: 120 cm²) filled with upland field soil, barnyardgrass (Ec), pale smartweed (Po), slender amaranth (Am), common lambsquarters (Ch) and rice flatsedge (Ci) were sown and covered with soil. A wettable powder prepared in accordance with Formulation Example 1 was diluted with water, and applied uniformly to the soil surface by a small-sized sprayer in an amount of 100 l/10 ares so as to apply 100 g of the active ingredient per 10 ares. The plants were then cultured in a green house, and the evaluation of the herbicidal effect was conducted on the 21th day after the treatment in accordance with the standard as identified in the above Table 4. The results are shown in the following Table 6.

TABLE 6

| Compound No. | Ec | Po | Am | Ch | Ci |
|---|---|---|---|---|---|
| 1 | 5 | 5 | 5 | 5 | 5 |
| 3 | 5 | 5 | 5 | 5 | 5 |
| 4 | 5 | 5 | 5 | 5 | 5 |
| 5 | 5 | 5 | 5 | 5 | 5 |
| 6 | 5 | 5 | 5 | 5 | 5 |
| 9 | 5 | 5 | 5 | 5 | 5 |
| 13 | 5 | 5 | 5 | 5 | 5 |
| 15 | 5 | 5 | 5 | 5 | 5 |
| 17 | 5 | 5 | 5 | 5 | 5 |
| 18 | 5 | 5 | 5 | 5 | 5 |
| 19 | 5 | 5 | 5 | 5 | 5 |
| 20 | 3 | 5 | 5 | 5 | 5 |
| 22 | 5 | 5 | 5 | 5 | 5 |
| 24 | 3 | 5 | 4 | 4 | 2 |
| 26 | 5 | 5 | 5 | 5 | 5 |
| 27 | 2 | 5 | 4 | 5 | 4 |
| 28 | 5 | 5 | 5 | 5 | 5 |
| 32 | 4 | 5 | 5 | 5 | 5 |
| 34 | 5 | 5 | 5 | 5 | 5 |
| 36 | 4 | 5 | 5 | 5 | 5 |
| 39 | 4 | 5 | 5 | 3 | 3 |
| 40 | 3 | 5 | 4 | 3 | 3 |
| 42 | 4 | 5 | 5 | 5 | 5 |
| 44 | 5 | 5 | 5 | 5 | 5 |
| 47 | 5 | 5 | 5 | 5 | 5 |
| 48 | 5 | 5 | 5 | 5 | 5 |
| 50 | 4 | 5 | 5 | 5 | 5 |
| 52 | 5 | 5 | 5 | 5 | 5 |
| 55 | 2 | 5 | 5 | 5 | 3 |
| 56 | 4 | 5 | 5 | 5 | 5 |
| 57 | 3 | 5 | 4 | 3 | 4 |
| 58 | 4 | 5 | 5 | 5 | 5 |
| 61 | 5 | 5 | 5 | 5 | 5 |
| 63 | 5 | 5 | 5 | 5 | 5 |
| 65 | 3 | 5 | 5 | 5 | 5 |

TABLE 6-continued

| Compound No. | Herbicidal effect | | | | |
|---|---|---|---|---|---|
| | Ec | Po | Am | Ch | Ci |
| 67 | 4 | 5 | 5 | 5 | 5 |
| 69 | 4 | 3 | 4 | 5 | 3 |
| 71 | 4 | 5 | 5 | 5 | 5 |
| 73 | 5 | 5 | 5 | 5 | 5 |
| 81 | 3 | 4 | 4 | 5 | 2 |
| 159 | 2 | 5 | 5 | 5 | 5 |
| 167 | 5 | 5 | 5 | 5 | 5 |
| 176 | 5 | 5 | 5 | 5 | 5 |
| 178 | 5 | 5 | 5 | 5 | 5 |
| 211 | 3 | 5 | 5 | 5 | 5 |
| 233 | 5 | 5 | 5 | 5 | 5 |
| 236 | 3 | 5 | 5 | 5 | 4 |
| (A) | 0 | 0 | 2 | 2 | 4 |
| (B) | 1 | 0 | 0 | 1 | 0 |
| (D) | 0 | 0 | 2 | 1 | 1 |

TEST EXAMPLE 3

(Herbicidal effect test by upland field foliage treatment)

In a plastic pot (surface area: 120 cm$^2$) filled with upland field soil, barnyardgrass (Ec), pale smartweed (Po), slender amaranth (Am), common lambsquarters (Ch) and rice flatsedge (Ci) were sown and covered with soil and were cultured in a green house for 2 weeks. A wettable powder prepared in accordance with Formulation Example 1 was diluted with water, and applied onto the foliages by a small-sized sprayer in an amount of 100 l/10 ares so as to apply 100 g of the active ingredient per 10 ares. The plants were then cultured in the green house, and the evaluation of the herbicidal effect was conducted on the 14th day after the treatment in accordance with the standard as identified in the above Table 4. The results are shown in the following Table 7.

TABLE 7

| Compound No. | Herbicidal effect | | | | |
|---|---|---|---|---|---|
| | Ec | Po | Am | Ch | Ci |
| 1 | 5 | 5 | 5 | 5 | 5 |
| 3 | 5 | 5 | 5 | 5 | 5 |
| 4 | 5 | 5 | 5 | 5 | 5 |
| 5 | 5 | 5 | 5 | 5 | 5 |
| 6 | 5 | 5 | 5 | 5 | 5 |
| 9 | 4 | 5 | 5 | 5 | 5 |
| 13 | 5 | 5 | 5 | 4 | 4 |
| 15 | 5 | 5 | 5 | 5 | 5 |
| 17 | 5 | 5 | 5 | 5 | 5 |
| 18 | 5 | 5 | 5 | 4 | 3 |
| 19 | 5 | 5 | 5 | 5 | 5 |
| 20 | 4 | 5 | 5 | 5 | 4 |
| 22 | 5 | 5 | 5 | 5 | 5 |
| 24 | 3 | 5 | 5 | 5 | 3 |
| 26 | 5 | 5 | 5 | 5 | 5 |
| 27 | 3 | 5 | 5 | 5 | 2 |
| 28 | 5 | 5 | 5 | 5 | 4 |
| 30 | 5 | 5 | 5 | 3 | 4 |
| 32 | 4 | 5 | 5 | 4 | 5 |
| 34 | 5 | 5 | 5 | 4 | 4 |
| 36 | 5 | 5 | 5 | 4 | 4 |
| 39 | 4 | 5 | 5 | 4 | 5 |
| 40 | 4 | 5 | 5 | 4 | 3 |
| 42 | 5 | 5 | 5 | 5 | 5 |
| 44 | 5 | 5 | 5 | 5 | 5 |
| 45 | 4 | 5 | 5 | 4 | 5 |
| 47 | 4 | 5 | 5 | 5 | 5 |
| 48 | 4 | 5 | 5 | 5 | 4 |
| 50 | 4 | 5 | 5 | 5 | 3 |
| 52 | 5 | 5 | 5 | 5 | 5 |
| 55 | 3 | 5 | 5 | 5 | 2 |
| 56 | 4 | 5 | 5 | 4 | 4 |
| 57 | 3 | 5 | 5 | 4 | 3 |
| 58 | 4 | 5 | 5 | 4 | 4 |
| 61 | 4 | 5 | 5 | 5 | 5 |

TABLE 7-continued

| Compound No. | Herbicidal effect | | | | |
|---|---|---|---|---|---|
| | Ec | Po | Am | Ch | Ci |
| 63 | 4 | 5 | 5 | 5 | 3 |
| 64 | 4 | 5 | 5 | 5 | 4 |
| 65 | 5 | 5 | 5 | 5 | 5 |
| 67 | 4 | 5 | 5 | 5 | 5 |
| 69 | 4 | 5 | 5 | 4 | 4 |
| 71 | 5 | 5 | 5 | 5 | 5 |
| 73 | 5 | 5 | 5 | 5 | 5 |
| 81 | 5 | 5 | 4 | 4 | 3 |
| 159 | 5 | 5 | 5 | 5 | 3 |
| 162 | 4 | 5 | 5 | 4 | 2 |
| 163 | 4 | 3 | 4 | 4 | 1 |
| 167 | 5 | 5 | 5 | 5 | 5 |
| 174 | 5 | 5 | 5 | 4 | 5 |
| 176 | 5 | 5 | 5 | 5 | 5 |
| 178 | 5 | 5 | 5 | 5 | 5 |
| 364 | 3 | 5 | 5 | 4 | 3 |
| 233 | 5 | 5 | 5 | 5 | 5 |
| 236 | 3 | 5 | 5 | 3 | 4 |
| (A) | 0 | 1 | 2 | 2 | 3 |
| (B) | 0 | 0 | 0 | 1 | 3 |
| (D) | 0 | 3 | 3 | 2 | 0 |
| (E) | 0 | 3 | 3 | 3 | 3 |

TEST EXAMPLE 4

(Herbicidal effect test and phytotoxicity test to rice by upland field foliage treatment)

In a plastic pot (surface area: 600 cm$^2$) filled with upland field soil, rice (Or), johnsongrass (So), Alopecurus aequalis (Al), pale smartweed (Po), slender amaranth (Am) and common lambsquarters (Ch) were sown and covered with soil, and were cultured in a green house for 2 weeks. A predetermined amount of a wettable powder prepared in accordance with Formulation Example 1 was diluted with 100 l of water per 10 ares, and was applied onto the foliages by a small-sized sprayer. The plants were then cultured in the green house, and the evaluation of the herbicidal effect and the phytotoxicity was conducted on the 14th day after the treatment in accordance with the standard as identified in the above Table 4. The results are shown in the following Table 8. The dose of active ingredient in the Table shows the amount of the active ingredient (g) per 10 ares.

TABLE 8

| Compound No. | Dose of active ingredient | Phytotoxicity Or | Herbicidal effect | | | | |
|---|---|---|---|---|---|---|---|
| | | | So | Al | Po | Am | Ch |
| 6 | 1.6 | 1 | 4 | 5 | 5 | 5 | 4 |
| 22 | 6.3 | 1 | 4 | 4 | 4 | 5 | 4 |
| 26 | 6.3 | 1 | 5 | 5 | 5 | 5 | 4 |
| 28 | 6.3 | 0 | 5 | 5 | 5 | 5 | 4 |
| 42 | 1.6 | 1 | 5 | 5 | 5 | 5 | 4 |
| 47 | 1.6 | 1 | 4 | 4 | 5 | 5 | 4 |
| 48 | 6.3 | 1 | 5 | 5 | 5 | 5 | 5 |
| 50 | 6.3 | 0 | 4 | 3 | 4 | 4 | 4 |
| 52 | 1.6 | 0 | 5 | 3 | 5 | 5 | 4 |
| 55 | 25.0 | 1 | 4 | 4 | 5 | 5 | 5 |
| 56 | 1.6 | 1 | 4 | 5 | 5 | 5 | 4 |
| 63 | 6.3 | 0 | 4 | 5 | 5 | 5 | 3 |
| 67 | 6.3 | 0 | 4 | 5 | 5 | 5 | 4 |
| 71 | 6.3 | 1 | 5 | 5 | 5 | 5 | 4 |
| 73 | 1.6 | 0 | 5 | 5 | 5 | 5 | 4 |
| 233 | 1.6 | 1 | 3 | 5 | 3 | 5 | 5 |
| (A) | 25.0 | 0 | 0 | 0 | 0 | 0 | 0 |
| (B) | 25.0 | 0 | 0 | 0 | 0 | 0 | 0 |
| (C) | 25.0 | 2 | 0 | 0 | 3 | 4 | 3 |
| (D) | 400.0 | 2 | 0 | 0 | 2 | 2 | 2 |
| (E) | 400.0 | 2 | 1 | 2 | 3 | 3 | 3 |

TEST EXAMPLE 5

(Herbicidal effect test and phytotoxicity test to rice by upland field soil treatment)

In a plastic pot (surface area: 600 cm$^2$) filled with upland field soil, rice (Or), johnsongrass (So), Alopecurus aequalis (Al), pale smartweed (Po), slender amaranth (Am) and common lambsquarters (Ch) were sown and covered with soil. After absorbing water from the bottom of the pot, a predetermined amount of a wettable powder prepared in accordance with Formulation Example 1 was diluted with 100 l of water per 10 ares, and was applied onto the soil surface by a small-sized sprayer. The plants were then cultured again in a green house, and the evaluation of the herbicidal effect and the phytotoxicity was conducted on the 20th day after the treatment in accordance with the standard as identified in the above Table 4. The results are shown in the following Table 9. The dose of active ingredient in the Table shows the amount of the active ingredient (g) per 10 ares.

TABLE 9

| Compound No. | Dose of active ingredient | Phytotoxicity Or | Herbicidal effect |||||
|---|---|---|---|---|---|---|---|
| | | | So | Al | Po | Am | Ch |
| 1 | 1.6 | 0 | 4 | 5 | 5 | 5 | 5 |
| 3 | 1.6 | 0 | 5 | 4 | 5 | 5 | 3 |
| 4 | 1.6 | 1 | 5 | 5 | 5 | 5 | 3 |
| 5 | 1.6 | 0 | 5 | 3 | 4 | 5 | 3 |
| 9 | 6.3 | 0 | 5 | 5 | 5 | 5 | 5 |
| 17 | 6.3 | 0 | 4 | 4 | 5 | 5 | 4 |
| 45 | 6.3 | 1 | 5 | 3 | 5 | 5 | 4 |
| 48 | 1.6 | 0 | 5 | 3 | 5 | 5 | 5 |
| 50 | 1.6 | 0 | 4 | 4 | 3 | 5 | 5 |
| 52 | 1.6 | 1 | 2 | 5 | 4 | 5 | 4 |
| 55 | 25.0 | 1 | 3 | 3 | 5 | 5 | 5 |
| 61 | 1.6 | 0 | 4 | 4 | 4 | 5 | 4 |
| 167 | 6.3 | 0 | 5 | 5 | 5 | 5 | 5 |
| 178 | 6.3 | 0 | 5 | 5 | 5 | 5 | 5 |
| 233 | 1.6 | 0 | 4 | 5 | 5 | 5 | 3 |
| (A) | 25.0 | 0 | 0 | 0 | 0 | 0 | 0 |
| (B) | 25.0 | 0 | 0 | 0 | 0 | 0 | 0 |
| (C) | 25.0 | 2 | 0 | 0 | 5 | 5 | 5 |
| (D) | 400.0 | 2 | 0 | 0 | 2 | 4 | 2 |
| (E) | 400.0 | 3 | 0 | 0 | 3 | 5 | 3 |

TEST EXAMPLE 6

(Herbicidal effect test and phytotoxicity test to wheat by upland field foliage treatment)

In a plastic pot (surface area: 600 cm$^2$) filled with upland field soil, wheat (Tr), johnsongrass (So), Alopecurus aequalis (Al), pale smartweed (Po), slender amaranth (Am) and common lambsquarters (Ch) were sown and covered with soil, and were cultured in a green house for 2 weeks. A predetermined amount of a wettable powder prepared in accordance with Formulation Example 1 was diluted with 100 l of water per 10 ares, and was applied onto the foliages by a small-sized sprayer. The plants were then cultured again in a green house, and the evaluation of the herbicidal effect and the phytotoxicity was conducted on the 14th day after the treatment in accordance with the standard as identified in the above Table 4. The results are shown in the following Table 10. The dose of active ingredient in the Table shows the amount of the active ingredient (g) per 10 ares.

TABLE 10

| Compound No. | Dose of active ingredient | Phytotoxicity Tr | Herbicidal effect |||||
|---|---|---|---|---|---|---|---|
| | | | So | Al | Po | Am | Ch |
| 6 | 6.3 | 0 | 5 | 5 | 5 | 5 | 4 |
| 9 | 6.3 | 0 | 5 | 5 | 5 | 5 | 5 |
| 17 | 1.6 | 1 | 5 | 5 | 5 | 5 | 4 |
| 22 | 25.0 | 0 | 4 | 4 | 5 | 5 | 5 |
| 26 | 6.3 | 0 | 5 | 5 | 5 | 5 | 4 |
| 28 | 6.3 | 0 | 5 | 5 | 5 | 5 | 4 |
| 42 | 1.6 | 1 | 5 | 5 | 5 | 5 | 4 |
| 44 | 6.3 | 1 | 5 | 5 | 5 | 5 | 5 |
| 47 | 6.3 | 1 | 5 | 5 | 5 | 5 | 5 |
| 48 | 6.3 | 1 | 5 | 5 | 5 | 5 | 5 |
| 50 | 6.3 | 0 | 4 | 3 | 4 | 4 | 4 |
| 52 | 1.6 | 0 | 5 | 3 | 5 | 5 | 4 |
| 56 | 25.0 | 1 | 5 | 5 | 5 | 4 | 4 |
| 63 | 6.3 | 1 | 4 | 5 | 5 | 5 | 3 |
| 67 | 6.3 | 0 | 4 | 5 | 5 | 5 | 4 |
| 71 | 1.6 | 0 | 4 | 5 | 5 | 5 | 4 |
| 73 | 1.6 | 1 | 5 | 5 | 5 | 5 | 4 |
| 233 | 6.3 | 0 | 4 | 5 | 5 | 5 | 5 |
| (A) | 25.0 | 0 | 0 | 0 | 0 | 0 | 0 |
| (B) | 25.0 | 0 | 0 | 0 | 0 | 0 | 0 |
| (C) | 25.0 | 2 | 0 | 0 | 3 | 4 | 3 |
| (D) | 400.0 | 2 | 0 | 0 | 2 | 2 | 2 |
| (E) | 400.0 | 2 | 1 | 2 | 3 | 3 | 3 |

TEST EXAMPLE 7

(Herbicidal effect test and phytotoxicity test to wheat by upland field soil treatment)

In a plastic pot (surface area: 600 cm$^2$) filled with upland field soil, wheat (Tr), johnsongrass (So), Alopecurus aequalis (Al), pale smartweed (Po), slender amaranth (Am) and common lambsquarters (Ch) were sown and covered with soil. After absorbing water from the bottom of the pot, a predetermined amount of a wettable powder prepared in accordance with Formulation Example 1 was diluted with 100 l of water per 10 ares, and was applied onto the soil surface by a small-sized sprayer. The plants were then cultured again in a green house, and the evaluation of the herbicidal effect and the phytotoxicity was conducted on the 20th day after the treatment in accordance with the standard as identified in the above Table 4. The results are shown in the following Table 11. The dose of active ingredient in the Table shows the amount of the active ingredient (g) per 10 ares.

TABLE 11

| Compound No. | Dose of active ingredient | Phytotoxicity Tr | Herbicidal effect |||||
|---|---|---|---|---|---|---|---|
| | | | So | Al | Po | Am | Ch |
| 1 | 1.6 | 0 | 4 | 5 | 5 | 5 | 5 |
| 3 | 1.6 | 0 | 5 | 4 | 5 | 5 | 3 |
| 4 | 1.6 | 0 | 5 | 5 | 5 | 5 | 3 |
| 5 | 1.6 | 0 | 5 | 5 | 5 | 5 | 3 |
| 9 | 6.3 | 0 | 5 | 5 | 5 | 5 | 5 |
| 17 | 6.3 | 1 | 4 | 4 | 5 | 5 | 4 |
| 22 | 6.3 | 1 | 5 | 5 | 4 | 5 | 5 |
| 28 | 25.0 | 1 | 5 | 5 | 5 | 5 | 5 |
| 42 | 6.3 | 0 | 5 | 5 | 5 | 5 | 5 |
| 44 | 1.6 | 0 | 5 | 5 | 5 | 5 | 5 |
| 45 | 6.3 | 0 | 5 | 3 | 5 | 5 | 4 |
| 47 | 1.6 | 0 | 5 | 3 | 5 | 5 | 5 |
| 48 | 6.3 | 1 | 5 | 5 | 5 | 5 | 5 |
| 50 | 6.3 | 0 | 5 | 5 | 5 | 5 | 5 |
| 55 | 25.0 | 1 | 3 | 3 | 5 | 5 | 5 |
| 56 | 25.0 | 1 | 5 | 5 | 5 | 5 | 3 |
| 167 | 6.3 | 0 | 5 | 5 | 5 | 5 | 5 |
| 178 | 6.3 | 0 | 5 | 5 | 5 | 5 | 5 |
| 233 | 6.3 | 0 | 4 | 5 | 5 | 5 | 3 |
| (A) | 25.0 | 0 | 0 | 0 | 0 | 0 | 0 |
| (B) | 25.0 | 0 | 0 | 0 | 0 | 0 | 0 |

TABLE 11-continued

| Compound No. | Dose of active ingredient | Phytotoxicity Tr | Herbicidal effect |||||
|---|---|---|---|---|---|---|---|
| | | | So | Al | Po | Am | Ch |
| (C) | 25.0 | 3 | 0 | 0 | 5 | 5 | 5 |
| (D) | 400.0 | 2 | 0 | 0 | 2 | 4 | 2 |
| (E) | 400.0 | 2 | 0 | 0 | 3 | 5 | 3 |

TEST EXAMPLE 8

(Herbicidal effect test and phytotoxicity test to the cotton by upland field foliage treatment)

In a plastic pot (surface area: 600 cm$^2$) filled with upland field soil, cotton (Go), johnsongrass (So), Alopecurus aequalis (Al), pale smartweed (Po), slender amaranth (Am) and common lambsquarters (Ch) were sown and covered with soil, and were cultured in a green house for 2 weeks. A predetermined amount of a wettable powder prepared in accordance with Formulation Example 1 was diluted with 100 l of water per 10 ares, and was applied onto the foliage by a small-sized sprayer. The plants were then cultured in the green house, and the evaluation of the herbicidal effect and the phytotoxicity was conducted on the 14th day after the treatment in accordance with the standard as identified in the above Table 4. The results are shown in the following Table 12. The dose of active ingredient in the Table shows the amount of the active ingredient (g) per 10 ares.

TABLE 12

| Compound No. | Dose of active ingredient | Phytotoxicity Go | Herbicidal effect |||||
|---|---|---|---|---|---|---|---|
| | | | So | Al | Po | Am | Ch |
| 17 | 1.6 | 1 | 5 | 5 | 5 | 5 | 4 |
| 55 | 25.0 | 1 | 4 | 4 | 5 | 5 | 5 |
| (A) | 100.0 | 2 | 0 | 0 | 2 | 3 | |
| (B) | 400.0 | 2 | 0 | 0 | 0 | 2 | 1 |

TEST EXAMPLE 9

(Herbicidal effect test and phytotoxicity test to cotton by upland field soil treatment)

In a plastic pot (surface area: 600 cm$^2$) filled with upland field soil, cotton (Go), johnsongrass (So), Alopecurus aequalis (Al), pale smartweed (Po), slender amaranth (Am) and common lambsquarters (Ch) were sown and covered with soil. After absorbing water from the bottom of the pot, a predetermined amount of a wettable powder prepared in accordance with Formulation Example 1 was diluted with 100 l of water per 10 ares, and was applied onto the soil surface by a small-sized sprayer. The plants were then cultured again in a green house, and the evaluation of the herbicidal effect and the phytotoxicity was conducted on the 20th day after the treatment in accordance with the standard as identified in the above Table 4. The results are shown in the following Table 13. The dose of active ingredient in the Table shows the amount of the active ingredient (g) per 10 ares.

TABLE 13

| Compound No. | Dose of active ingredient | Phytotoxicity Go | Herbicidal effect |||||
|---|---|---|---|---|---|---|---|
| | | | So | Al | Po | Am | Ch |
| 1 | 1.6 | 0 | 4 | 5 | 5 | 5 | 5 |
| 3 | 1.6 | 1 | 5 | 4 | 5 | 5 | 3 |
| 4 | 1.6 | 1 | 5 | 5 | 5 | 5 | 3 |
| 5 | 1.6 | 1 | 5 | 3 | 4 | 5 | 3 |
| 9 | 1.6 | 0 | 4 | 5 | 4 | 5 | 4 |
| 19 | 6.3 | 1 | 3 | 5 | 5 | 5 | 5 |
| 28 | 25.0 | 1 | 5 | 5 | 5 | 5 | 5 |
| 44 | 1.6 | 0 | 5 | 5 | 5 | 5 | 5 |
| 48 | 1.6 | 1 | 5 | 3 | 5 | 5 | 5 |
| 50 | 1.6 | 0 | 4 | 4 | 3 | 5 | 5 |
| 52 | 1.6 | 0 | 2 | 5 | 4 | 5 | 4 |
| 55 | 25.0 | 0 | 3 | 3 | 5 | 5 | 5 |
| 61 | 1.6 | 0 | 4 | 4 | 4 | 5 | 4 |
| 167 | 6.3 | 0 | 5 | 5 | 5 | 5 | 5 |
| 178 | 1.6 | 1 | 4 | 4 | 5 | 5 | 4 |
| 233 | 1.6 | 1 | 4 | 5 | 5 | 5 | 3 |
| (A) | 400.0 | 2 | 0 | 0 | 1 | 4 | 2 |
| (B) | 400.0 | 2 | 1 | 0 | 0 | 3 | 2 |
| (C) | 25.00 | 2 | 0 | 0 | 5 | 5 | 5 |
| (D) | 400.0 | 3 | 0 | 0 | 2 | 4 | 2 |
| (E) | 400.0 | 2 | 0 | 0 | 3 | 5 | 3 |

We claim:
1. A compound having the following formula or a herbicidally acceptable salt thereof:

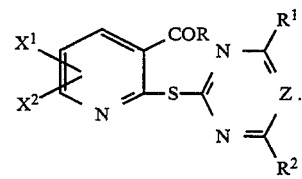

wherein R is selected from the group consisting of a hydrogen atom, a hydroxyl group, a $C_1 \sim C_7$ alkoxy group, a $C_1 \sim C_7$ alkoxy group, a pivaloyloxymethoxy group, a benzyloxy group, a benzyloxy group substituted with a chlorine atom or a methoxy group, a trimethylsilylethoxy group, a methylsulfonylamino group, a methylthio group, a phenoxy group and a phenylthio group;

$R^1$ and $R^2$ are the same or different, and are selected from the group consisting of a hydrogen atom, a $C_1 \sim C_7$ alkoxy group, a halogen atom, a $C_1 \sim C_3$ alkylamino group, a di $C_1 \sim C_3$ alkylamino group, a halo $C_1 \sim C_7$ alkoxy group and a $C_1 \sim C_7$ alkyl group;

Z is a methine group;

$X^1$ is selected from the group consisting of a benzoylamino group, a cyclo $C_3 \sim C_7$ alkyl group, halo $C_1 \sim C_7$ alkoxy group, a $C_2 \sim C_8$ alkenyloxy group, a $C_2 \sim C_8$ alkynyloxy group, a methoxycarbonyl group, a $C_1 \sim C_3$ alkylamino group, a di $C_1 \sim C_3$ alkylamino group, a phenyl group, a phenyl group substituted with substituent selected from the group consisting of a lower alkyl group, a halogen atom, a nitro group, a halo $C_1 \sim C_7$ alkyl group, a halo $C_1 \sim C_7$ alkoxy group, a $C_1 \sim C_7$ alkoxy group, a piperidino group, a di $C_1 \sim C_3$ alkylamino group, a phenoxy group, a methylphenoxy group, a an ethoxymethoxy group, a methoxyethoxy group, a methoxymethoxy group, a cyano group, an ethynyl group, a $C_1 \sim C_3$ alkylamino group, a ethoxycarbonyl $C_1 \sim C_2$ alkoxy group, a methoxymethyl group, a $C_1 \sim C_2$ alkylthio $C_1 \sim C_2$ alkoxy group, a benzyloxy group and a hydroxyl group; a benzyl group; a benzyl group substituted with a chlorine atom, a benzyloxy group, and a benzylthio group; a phenoxy group; a phenoxy group substituted with a substituent selected from the group consisting of a halogen atom, a methyl group and a methoxy group; a phenylthio group; a phenylthio group substituted with a substituent selected from the group consisting of a chlorine atom, a methyl group and a methoxy group; a $C_1 \sim C_2$ alkoxyimino $C_1 \sim C_2$ alkyl group, a $C_2 \sim C_3$ acyl group, a $C_1 \sim C_2$ alkylthio group, a phenylamino group; a phenylamino group substituted with a chlorine atom; a carboxyl group, and a group having the formula,

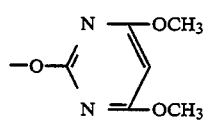

$X^2$ is selected from the group consisting of a hydrogen atom, halogen atom, a $C_1 \sim C_2$ alkyl group, a methoxy group, and a di methylamino group.

2. The compound or salt according to claim 1, wherein R is selected from the group consisting of a hydrogen atom, a hydroxyl group, a $C_1 \sim C_7$ alkoxy group, a benzyloxy group, a benzyloxy group substituted with a chlorine atom or a methoxy group; a methylsulfonylamino group, a methylthio group, and a phenylthio group;

$R^1$ and $R^2$ are the same or different, and are selected from the group consisting of a hydrogen atom, a $C_1 \sim C_7$ alkoxy group, a halogen atom, a halo $C_1 \sim C_7$ alkoxy group, and a $C_1 \sim C_7$ alkyl group;

Z is a methine group;

$X^1$ is selected from the group consisting of a benzoylamino group, a cyclo $C_3 \sim C_7$ alkyl group, halo $C_1 \sim C_7$ alkoxy group, a $C_2 \sim C_8$ alkenyloxy group, a $C_2 \sim C_8$ alkynyloxy group, a methoxycarbonyl group, a phenyl group, a phenyl group substituted with a substituent selected from the group consisting of a lower alkyl group, a halogen atom, a nitro group, a halo $C_1 \sim C_7$ alkyl group, a halo $C_1 \sim C_7$ alkoxy group, a $C_1 \sim C_7$ alkoxy group, a piperidino group, a di $C_1 \sim C_3$ alkylamino group, a phenoxy group, a methylphenoxy group, an ethoxymethoxy group, a methoxymethoxy group, a methoxyethoxy group, a cyano group, an ethynyl group, a $C_1 \sim C_3$ alkylamino group, a ethoxycarbonyl $C_1 \sim C_2$ alkoxy group, a methoxymethyl group, a $C_1 \sim C_2$ alkylthio $C_1 \sim C_2$ alkoxy group, a benzyloxy group and a hydroxyl group; a benzyl group, a benzyloxy group, a benzylthio group, a benzyl group which is substituted with a chlorine atom; a phenoxy group; a phenoxy group substituted with a substituent selected from the group consisting of a halogen atom, a methyl group and a methoxy group; a phenylthio group; a phenylthio group substituted with a substituent selected from the group consisting of a chlorine atom, a methyl group and a methoxy group; a $C_1 \sim C_2$ alkoxyimino $C_1 \sim C_2$ alkyl group, a $C_2 \sim C_3$ acyl group, a $C_1 \sim C_2$ alkylthio group, a phenylamino group; a phenylamino group substituted with a chlorine atom; a carboxyl group, a benzoylamino group and a 4,6 di methoxypyrimidinylthio group;

$X^2$ is selected from the group consisting of a hydrogen atom, a chlorine atom, a $C_1 \sim C_2$ alkyl group, a methoxy group and a di methylamino group.

3. The compound or salt according to claim 1, wherein $X^1$ is selected from the group consisting of a cyclo $C_3 \sim C_7$ alkyl group, a halo $C_1 \sim C_7$ alkoxy group, a $C_2 \sim C_8$ alkynyloxy group, a methoxycarbonyl group, a phenyl group, a phenyl group substituted with subsitutent selected from the group consisting of a lower alkyl group, a halogen atom, a nitro group, a halo $C_1 \sim C_7$ alkyl group, a halo $C_1 \sim C_7$ alkoxy group, a $C_1 \sim C_7$ alkoxy group, a piperidino group, a di $C_1 \sim C_3$ alkylamino group, a phenoxy group, a methylphenoxy group, a methoxyethoxy group, a methoxymethoxy group, an ethoxymethoxy group a cyano group, a an ethynyl group, a $C_1 \sim C_3$ alkylamino group, a ethoxycarbonyl $C_1 \sim C_2$ alkoxy group, a methoxymethyl group, a $C_1 \sim C_2$ alkylthio $C_1 \sim C_2$ alkoxy group, a benzyloxy group and a hydroxyl group; a benzyloxy group, a benzylthio group, a benzyl group; a benzyl group substituted with a chlorine atom; a phenoxy group; a phenoxy group substituted with a substituent selected from the group consisting of a halogen atom, a methyl group and a methoxy group; a phenylthio group; a phenylthio group substituted with a substituent selected from the group consisting of a chlorine atom, a methyl group and a methoxy group; a $C_1 \sim C_2$ alkoxyimino $C_1 \sim C_2$ alkyl group, a $C_2 \sim C_3$ acyl group, a $C_1 \sim C_2$ alkylthio group, a phenylamino group, a phenylamino group substituted with a chlorine atom, a carboxyl group, a benzoylamino group and a group having the formula,

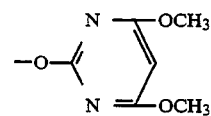

$X^2$ is selected from the group consisting of a hydrogen atom, a chlorine atom, a $C_1 \sim C_2$ alkyl group, a methoxy group and a di methylamino group.

4. A compound having the following formula or a herbicidally acceptable salt thereof:

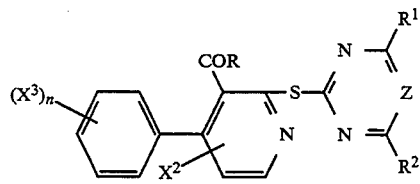

wherein R is selected from the group consisting of a hydrogen atom, a hydroxyl group, a $C_1 \sim C_7$ alkoxy group, a $C_1 \sim C_7$ alkoxy $C_1 \sim C_7$ alkoxy group, a pivaloylmethoxy group, a benzyloxy group, a benzyloxy group substituted with a substituent selected from the group consisting of a chlorine atom or a methoxy group; a trimethylsilylethoxy group, a methylsulfonylamino group, a $C_1 \sim C_2$ alkylthio group, a phenoxy group and a phenylthio group;

$R^1$ and $R^2$ are the same or different, and are selected from the group consisting of a hydrogen atom, a $C_1 \sim C_7$ alkoxy group, a halogen atom, a $C_1 \sim C_3$ alkylamino group, a di $C_1 \sim C_3$ alkylamino group, a halo $C_1 \sim C_7$ alkoxy group and a $C_1 \sim C_7$ alkyl group;

Z is a methine group;

X³ is selected from the group consisting of a halogen atom, a $C_1 \sim C_7$ alkyl group, a $C_1 \sim C_7$ alkoxy group, a $C_1 \sim C_3$ alkylamino group, a di $C_1 \sim C_3$ alkylamino group, a halo $C_1 \sim C_7$ alkyl group, a halo $C_1 \sim C_7$ alkoxy group, a nitro group, a hydroxyl group, a di $C_1 \sim C_7$ alkoxy group, a methoxycarbonyl $C_1 \sim C_2$ alkoxy group, a $C_1 \sim C_2$ alkylthio $C_1 \sim C_2$ alkoxy group, a benzyloxy group, a cyano group, a phenoxy group, a $C_1 \sim C_2$ alkylthio group, a methoxymethyl group, a $C_2 \sim C_8$ alkenyl group and a $C_2 \sim C_8$ alkynyl group;

X² is selected from the group consisting of a hydrogen atom, a halogen atom, a $C_1 \sim C_2$ alkyl group, a methoxy group, and a di methylamino group;

and n is 0 or an integer of 1 to 3, and X³ can be a combination of different groups when n is at least 2.

5. The compound or salt according to claim 4, wherein X² is selected from the group consisting of a hydrogen atom, a $C_1 \sim C_2$ alkyl group, a methoxy group, a halogen atom, a methylamino group, and a di methylamino group.

6. A compound having the following formula or a herbicidally acceptable salt thereof:

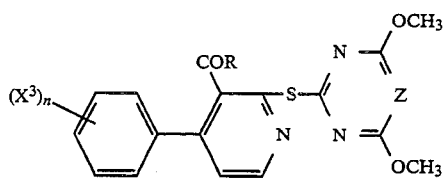

wherein R is selected from the group consisting of a hydroxyl group, a $C_1 \sim C_7$ alkoxy group, a di $C_1 \sim C_7$ alkoxy group, a pivaloyloxymethyl group, a benzyloxy group, a benzyloxy group substituted with a chlorine atom or a methoxy group; a trimethylsilylethoxy group, a methylsulfonylamino group, a $C_1 \sim C_2$ alkylthio group and a phenoxy group;

Z is a methine group;

X³ is selected from the group consisting of a halogen atom, a $C_1 \sim C_7$ alkyl group, a $C_1 \sim C_7$ alkoxy group, a $C_1 \sim C_3$ alkylamino group, a di $C_1 \sim C_3$ alkylamino group, a halo $C_1 \sim C_7$ alkyl group, a halo $C_1 \sim C_7$ alkoxy group, a nitro group, a hydroxyl group, a $C_1 \sim C_7$ alkoxy $C_1 \sim C_7$ alkoxy group, a methoxycarbonyl $C_1 \sim C_2$ alkoxy group, a $C_1 \sim C_2$ alkylthio $C_1 \sim C_2$ alkoxy group, a benzyloxy group, a cyano group, a phenoxy group, a $C_1 \sim C_2$ alkylthio group, a methoxymethyl group, a $C_2 \sim C_8$ alkenyl group and a $C_2 \sim C_8$ alkynyl group;

n is 0 or an integer of 1 to 3, and X³ can be a combination of different groups when n is at least 2.

7. An herbicidal composition comprising a herbicidally effective amount of the compound or a salt thereof as defined in claim 1 and an agriculturally acceptable adjuvant.

8. A method for killing weeds which comprises applying an herbicidally effective amount of the compound or a salt thereof as defined in claim 1 to a locus to be protected.

9. 4-(4-chlorophenyl)-2-(4,6-dimethoxypyrimidin-2-yl thio)nicotinic acid.

* * * * *

UNITED STATES PATENT AND TRADEMARK OFFICE
CERTIFICATE OF CORRECTION

PATENT NO. : 5,380,700
DATED : January 10, 1995
INVENTOR(S) : Masahiro MIYAZAKA, et al.

It is certified that error appears in the above-indentified patent and that said Letters Patent is hereby corrected as shown below:

On the title page, Item [30], the PCT information has been omitted from the Foreign Application Priority Data. It should read:

--Mar. 26, 1992 [PCT] PCT.....PCT/JP92/00362--

Signed and Sealed this

Thirteenth Day of June, 1995

Attest:

BRUCE LEHMAN

Attesting Officer    Commissioner of Patents and Trademarks